(12) United States Patent
Wilson

(10) Patent No.: US 12,697,177 B2
(45) Date of Patent: Aug. 4, 2026

(54) TOOL DRIVER AXIAL DISPLACEMENT SENSING

(71) Applicant: Auris Health, Inc., Redwood City, CA (US)

(72) Inventor: Colin Allen Wilson, Burlingame, CA (US)

(73) Assignee: Auris Health, Inc., Redwood City, CA (US)

( * ) Notice: Subject to any disclaimer, the term of this patent is extended or adjusted under 35 U.S.C. 154(b) by 229 days.

(21) Appl. No.: 18/581,249

(22) Filed: Feb. 19, 2024

(65) Prior Publication Data

US 2024/0293185 A1 Sep. 5, 2024

Related U.S. Application Data

(60) Provisional application No. 63/449,745, filed on Mar. 3, 2023.

(51) Int. Cl.
*A61B 34/20* (2016.01)
*A61B 34/00* (2016.01)

(52) U.S. Cl.
CPC .............. *A61B 34/20* (2016.02); *A61B 34/71* (2016.02); *A61B 2034/731* (2016.02); *A61B 2562/228* (2013.01)

(58) Field of Classification Search
None
See application file for complete search history.

(56) References Cited

U.S. PATENT DOCUMENTS

| | | | |
|---|---|---|---|
| 9,763,741 B2 | 9/2017 | Alvarez et al. | |
| 10,905,513 B2 | 2/2021 | Scheib et al. | |
| 10,912,544 B2 | 2/2021 | Brisson et al. | |
| 11,026,758 B2 | 6/2021 | Mintz et al. | |
| 2011/0028894 A1* | 2/2011 | Foley ............... | A61M 25/0136 604/95.01 |
| 2017/0172549 A1 | 6/2017 | Smaby et al. | |
| 2018/0116738 A1 | 5/2018 | Bajo et al. | |
| 2020/0297437 A1* | 9/2020 | Schuh ................. | A61G 13/101 |
| 2021/0045826 A1 | 2/2021 | Asadian et al. | |
| 2021/0137621 A1 | 5/2021 | Ummalaneni et al. | |
| 2023/0063521 A1* | 3/2023 | Yu .......................... | B25J 9/1633 |

OTHER PUBLICATIONS

International Search Report and Written Opinion dated Jun. 3, 2024, for International Application No. PCT/IB2024/051949, 9 pages.

* cited by examiner

*Primary Examiner* — Michael W Kahelin
(74) *Attorney, Agent, or Firm* — FBT Gibbons LLP

(57) ABSTRACT

A tool driver for a robotic system can include a sensor to allow the surgical robotic system to determine if a tool or a sterile adapter are fully coupled to the tool driver. The tool driver can include a rotating output that can manipulate a tool and translate perpendicular to a surface of a tool driver body. The tool driver can include a drive mechanism to rotate the rotating output.

21 Claims, 27 Drawing Sheets

TOOL DRIVER AXIAL DISPLACEMENT SENSING

CROSS-REFERENCE TO RELATED APPLICATIONS

This application claims priority to U.S. Provisional Application No. 63/449,745 filed Mar. 3, 2023 by Colin Allen Wilson entitled, "Tool Driver Axial Displacement Sensing", which is incorporated by reference herein as if reproduced in its entirety.

TECHNICAL FIELD

Systems and methods disclosed herein related to robotic systems, and more particularly to displacement sensing for robotic systems.

BACKGROUND

Minimally invasive procedures allow for access to a targeted site within a patient with minimal trauma to the patient. A medical robotic system can provide a mechanism through which one or more robotic arms are used to perform a surgical operation. For example, laparoscopic surgery can allow for surgical access to a patient's cavity through a small incision on the patient's abdomen.

The robotic arms of the robotic system can be coupled to one or more tools, such as a cannula or other devices, that will be used to perform the surgical operation on a patient. Each robotic arm can include an instrument or tool driver to engage with a respective surgical tool. In some applications, surgical tools and/or sterile adapters can be attached or otherwise coupled to the tool driver by sliding or placing the tool or adapter along a surface of the tool driver into engagement.

The tool driver can include one or more rotating outputs to manipulate or otherwise operate the surgical tool. The rotating outputs may be keyed to the mating inputs of the sterile adapter or the tool to allow for the transmission of torque.

The rotating outputs of the tool driver can retract axially to allow for the tool or a sterile adapter to slide along the surface of the tool driver to be coupled. The rotating outputs can extend axially to engage the mating inputs of the tool or sterile adapter upon proper engagement with the tool driver. In some applications, the rotating outputs can be rotated to align the keyed portions of the rotating outputs and the corresponding rotating inputs to allow for operation after attachment of the sterile adapter and tool to the tool driver.

SUMMARY

Some predicate systems may operate by assuming that the rotating outputs would be rotationally aligned and fully engaged with the rotating inputs of the sterile adapter after a predetermined number of rotations of the rotating outputs. Further, certain predicate systems may first lock or otherwise prevent rotation of the rotating inputs of the sterile adapter and then detect an increase in motor current when the rotating outputs engage with the locked rotating inputs of the sterile adapter. Similarly, certain predicate systems may detect an increase in motor current when the rotating outputs engage with the rotating inputs of the attached tool.

In accordance with some embodiments disclosed herein is the realization that as robotic systems developed by the present Applicant continue to evolve and provide functionality hitherto unavailable, important and unexpected changes to the structure and architecture of the robotic system were discovered and found to provide surprisingly important and advantageous results in facilitating the effective and simple operations of the robotic system. Further, in accordance with some embodiments disclosed herein is the realization that faster and more accurate confirmation of engagement between the tool driver and the sterile adapter and/or the surgical tool is desired. As such, the present disclosure addresses these and other challenges.

For example, due to the unique architecture of embodiments of robotic systems developed by the present Applicant, unique and innovative architecture has made it possible for the robotic system to more quickly and more accurately determine if the sterile adapter and/or the surgical tool is properly attached to the tool driver. As a result, the robotic system can prevent operation until the sterile adapter and the surgical tool are properly attached. Further, the robotic system can confirm engagement or identify malfunctions of each of the individual rotating outputs of the tool driver.

Accordingly, embodiments disclose herein provide a tool driver that incorporates a sensor to determine an axial position of the rotating output of the tool driver. In addition to determining the axial position of the rotating output, the sensor of the tool driver can be utilized to rapidly determine if the rotating output, and in turn, the tool driver is properly engaged to the sterile adapter and the surgical tool.

Advantageously, some embodiments of the sensor arrangement disclosed herein can allow for the robotic system and/or the user to determine if the sterile adapter or the tool is properly attached to the tool driver. Moreover, the robotic system can confirm engagement or identify malfunctions of each of the individual rotating outputs of the tool driver. Such sensor arrangements can provide a solution to the above-noted challenges and have not been disclosed or implemented in predicate systems given that such systems did not implement or otherwise contemplate the unique improvements of Applicant's new technology until the discovery and development of embodiments of the sensor arrangements described herein.

In accordance with some embodiments, the tool driver includes a motor coupled to the rotating output. The rotating output can include a disk extending from the body of the tool driver to engage with the input of the surgical tool. The disk can define a keyed portion.

In some embodiments, the tool driver includes a biasing member to urge the rotating output into engagement with the sterile adapter and/or the surgical tool.

In some embodiments, the sensor can be implemented as an inductive sensor and/or an optical sensor. Embodiments of the sensor implemented as an inductive sensor can include a ferrous component coupled to the rotating output and a conductive coil to provide a signal corresponding to the movement of the ferrous component and therefore the rotating output. Embodiments of the sensor implemented as an optical sensor can include a rotating output with a reflective surface that provides a signal to the optical sensor.

In some embodiments, the tool driver can include a translatable peg to space apart the sterile adapter from the tool driver.

In some embodiments, the tool driver includes multiple rotating outputs.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart

Figure 1:
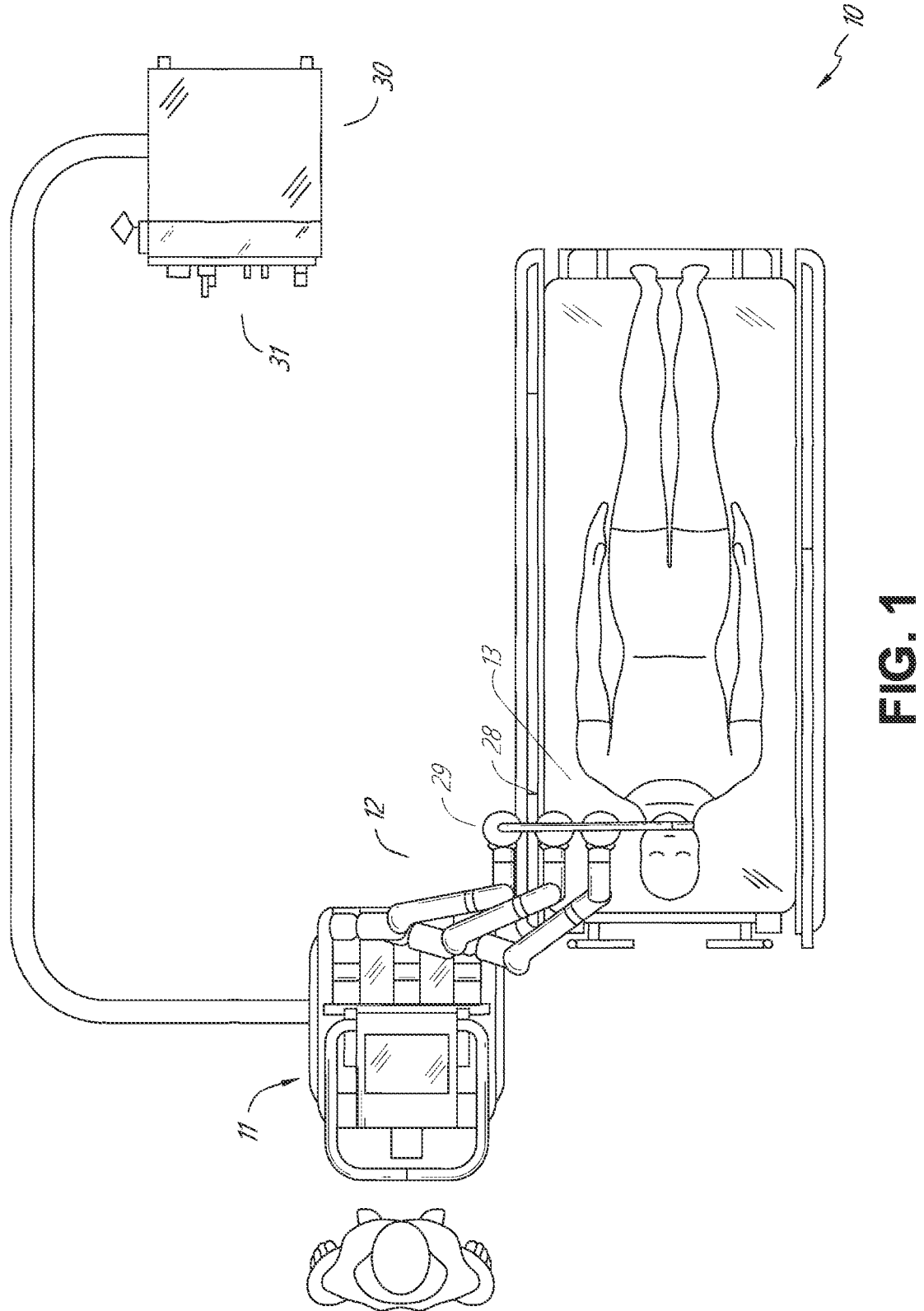
FIG. 1 illustrates an embodiment of a cart-based robotic system arranged for diagnostic and/or therapeutic bronchoscopy procedure(s).
Figure 2:
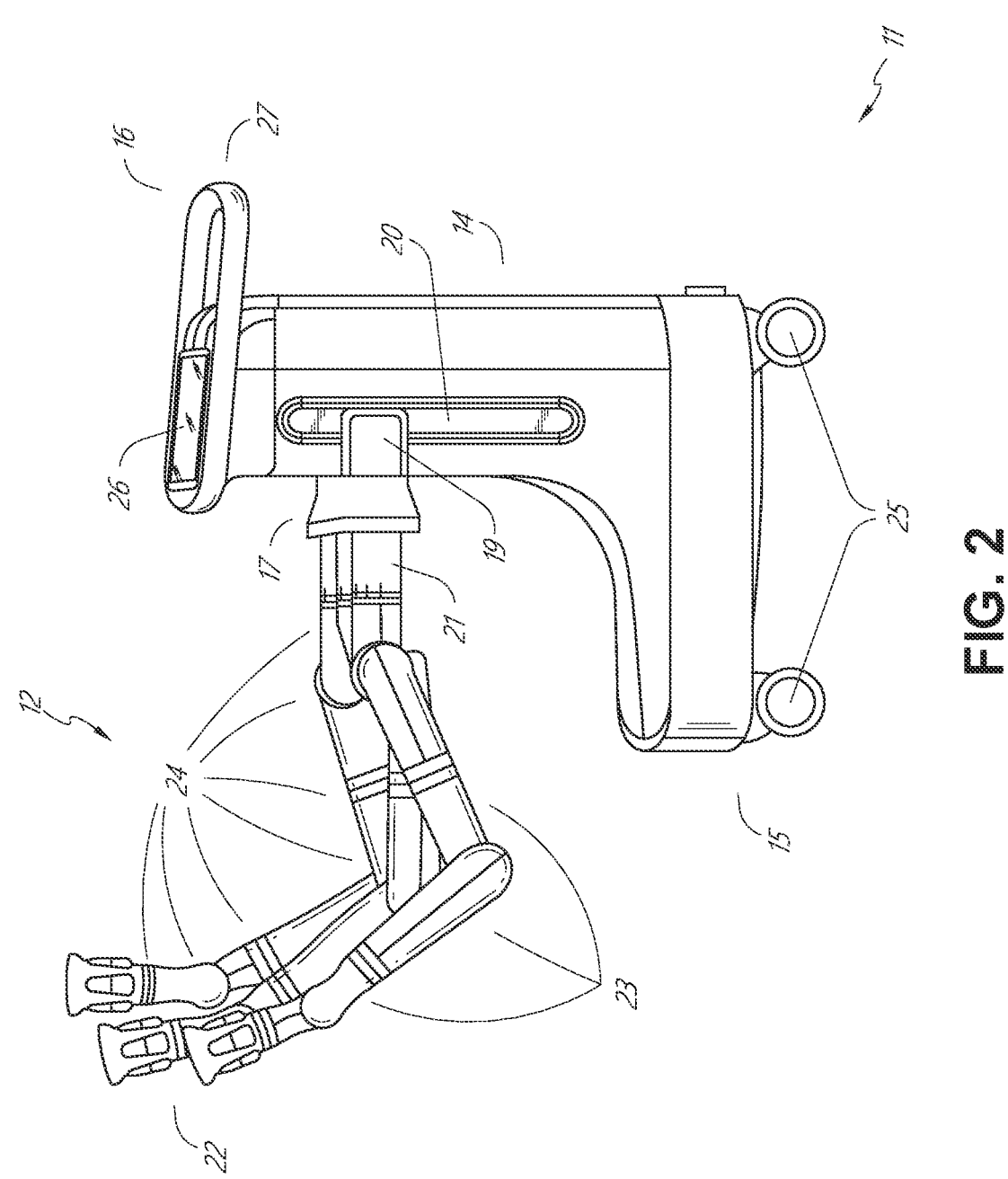
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
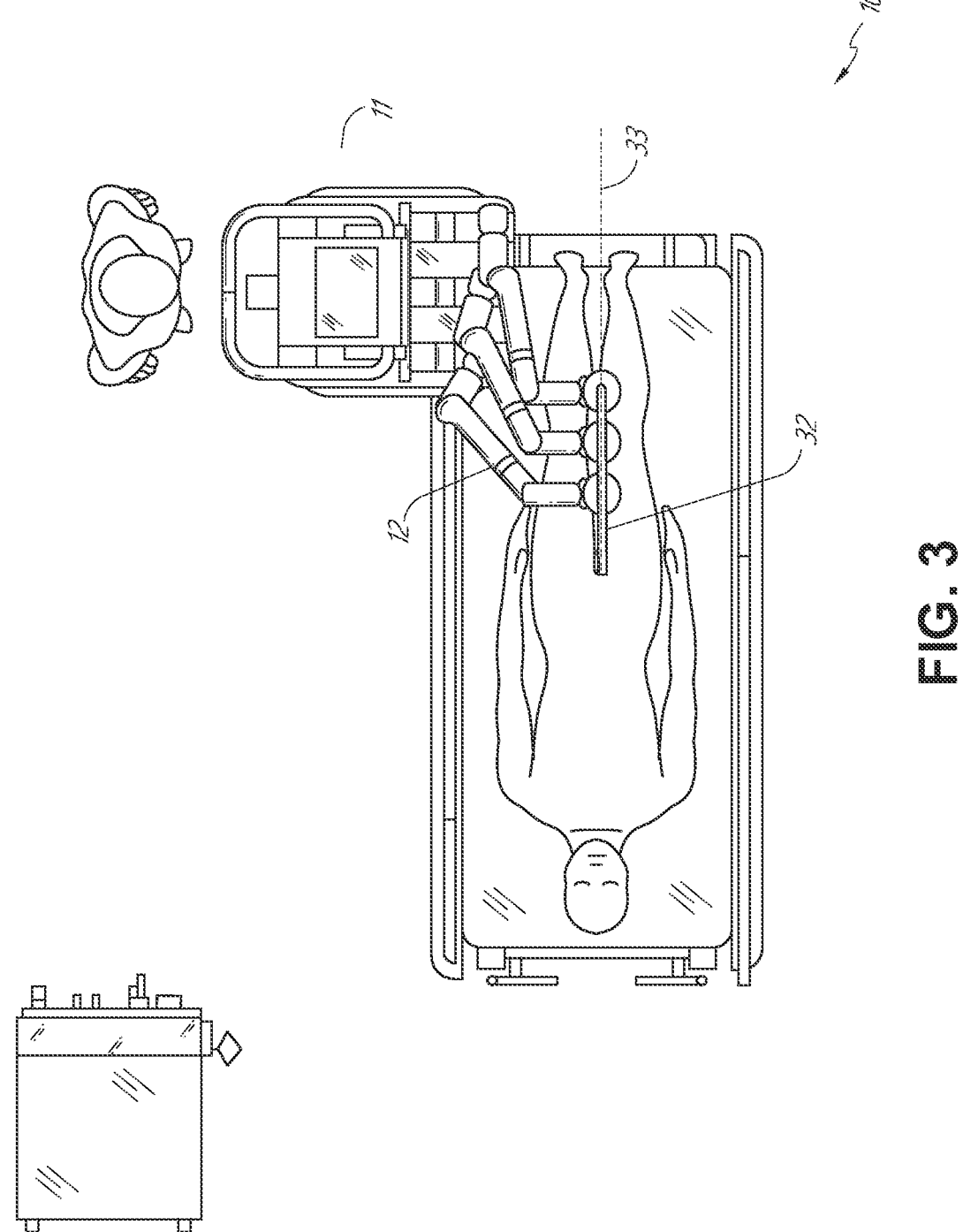
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
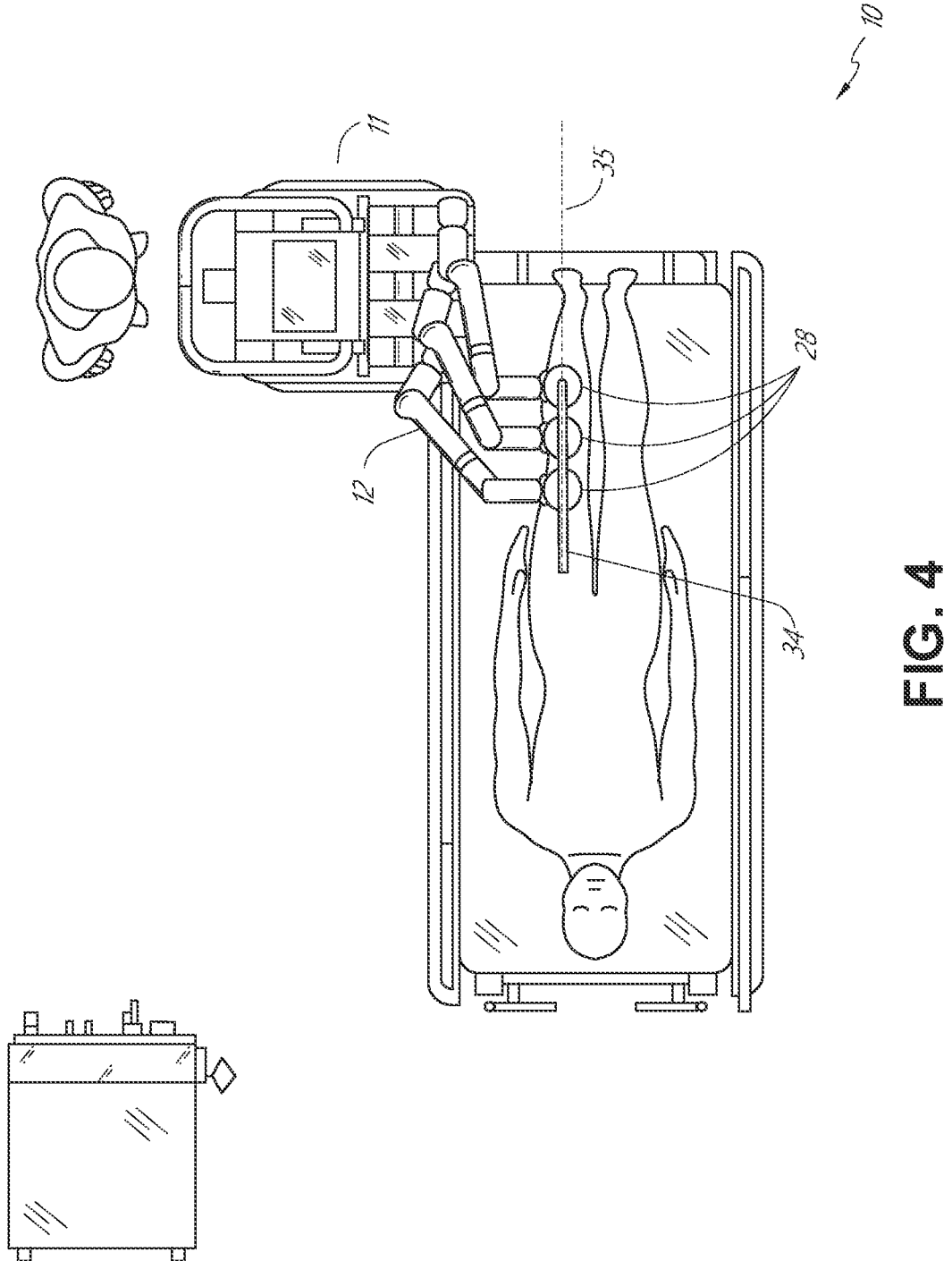
FIG. 4 illustrates an embodiment of the robotic system of FIG. 1 arranged for a vascular procedure.

FIG. 4 illustrates an embodiment of a robotically enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table

Figure 5:
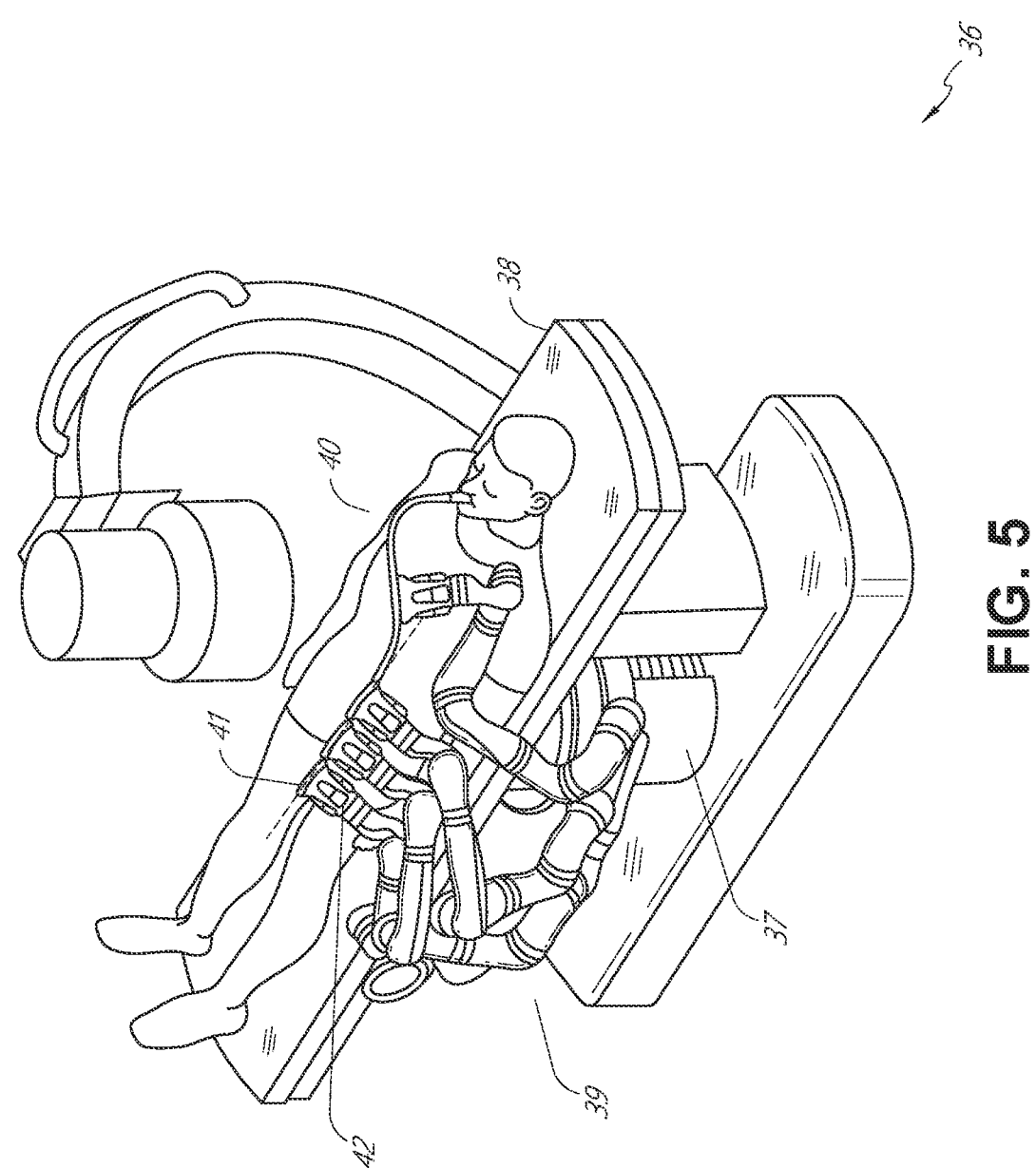
FIG. 5 illustrates an embodiment of a table-based robotic system arranged for a bronchoscopy procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
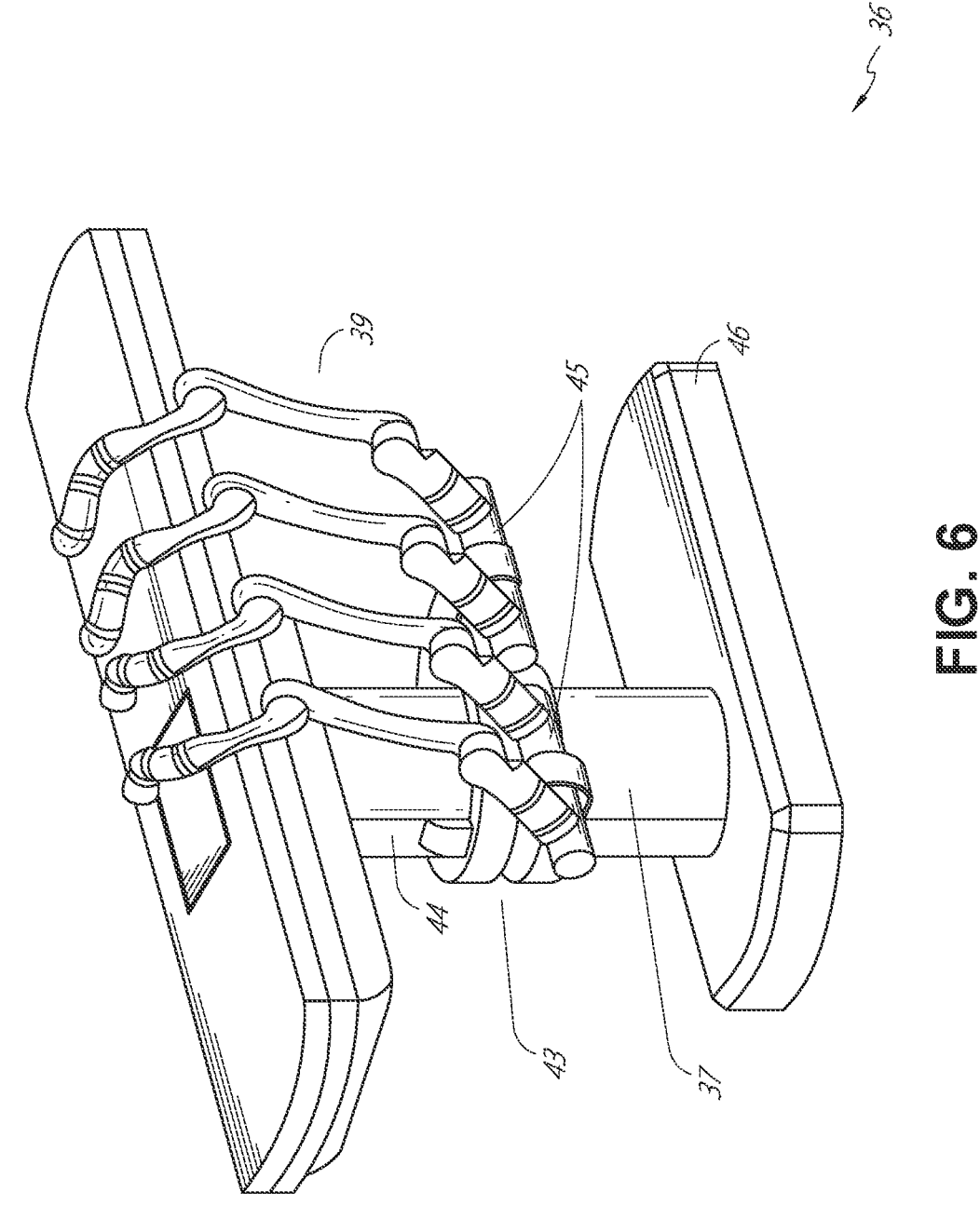
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
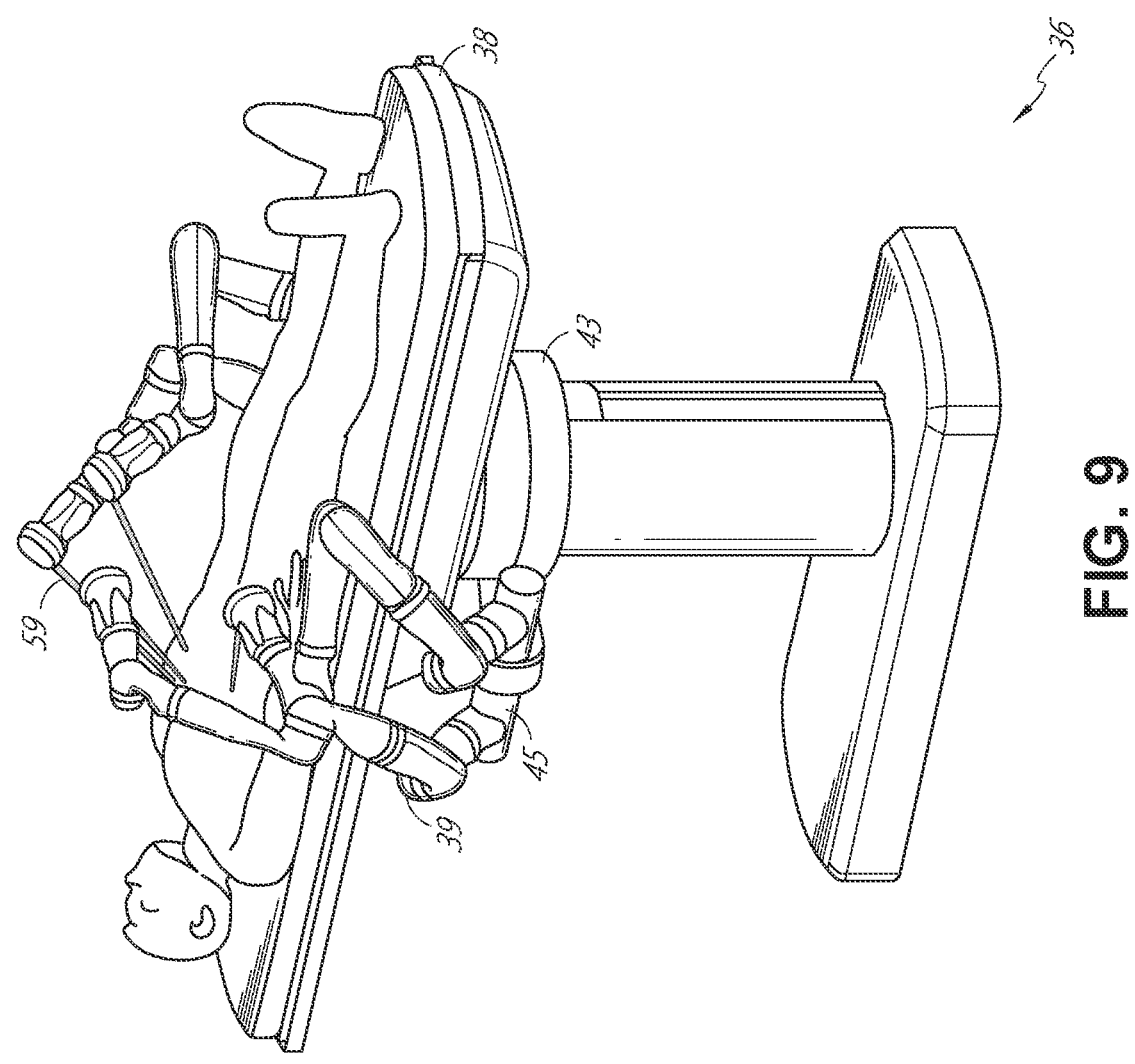
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
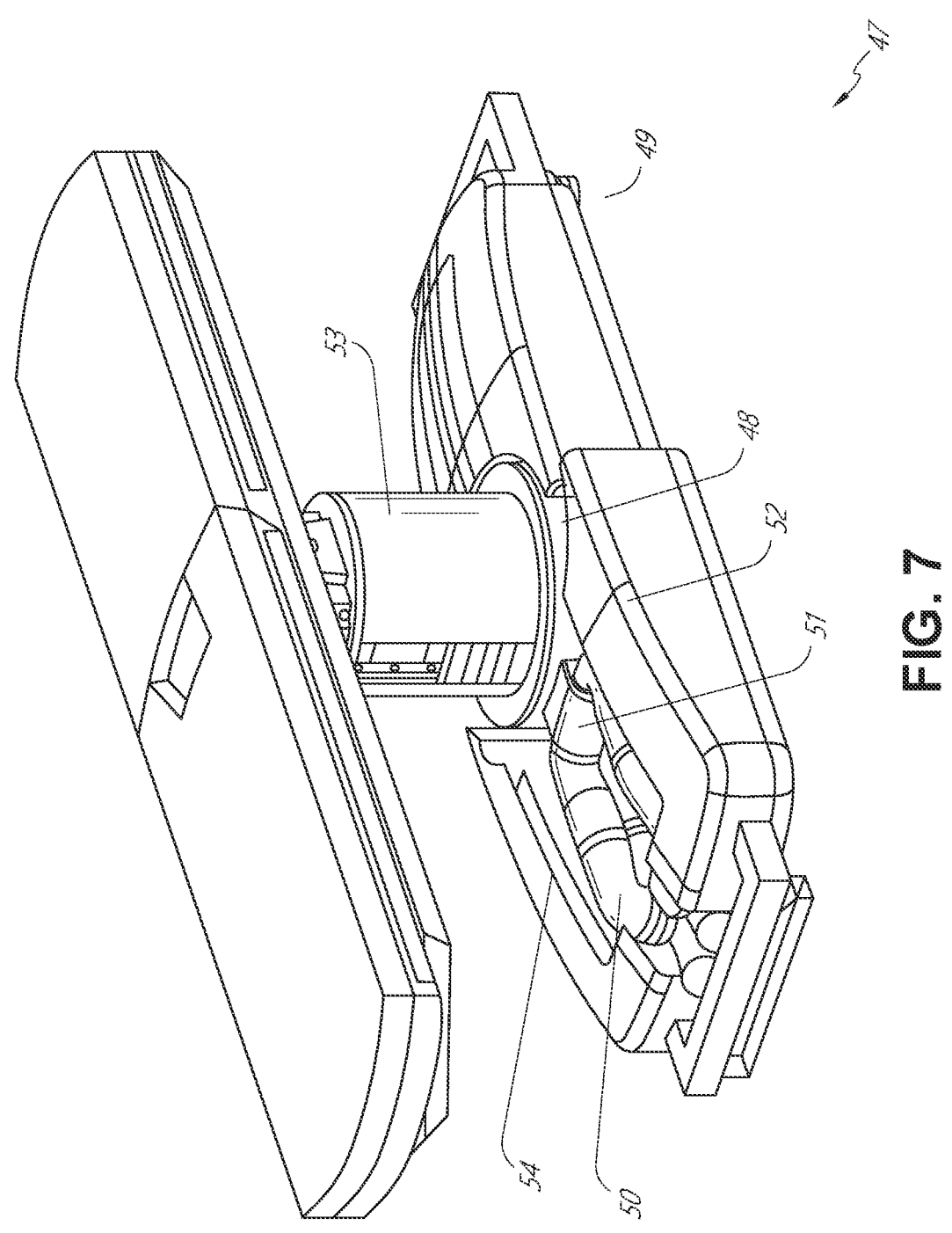
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
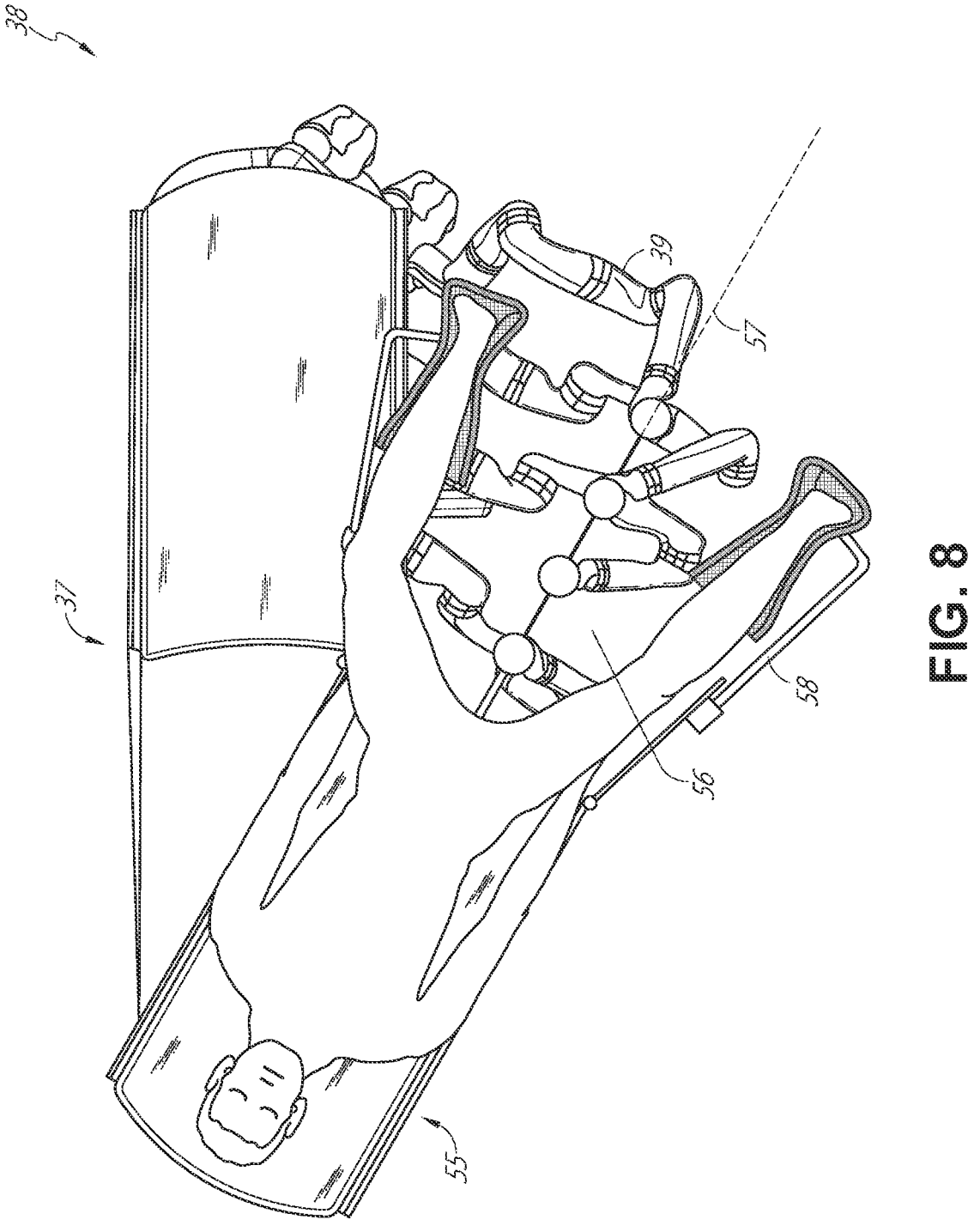
FIG. 8 illustrates an embodiment of a table-based robotic system configured for a ureteroscopy procedure.

FIG. 8 illustrates an embodiment of a robotically enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
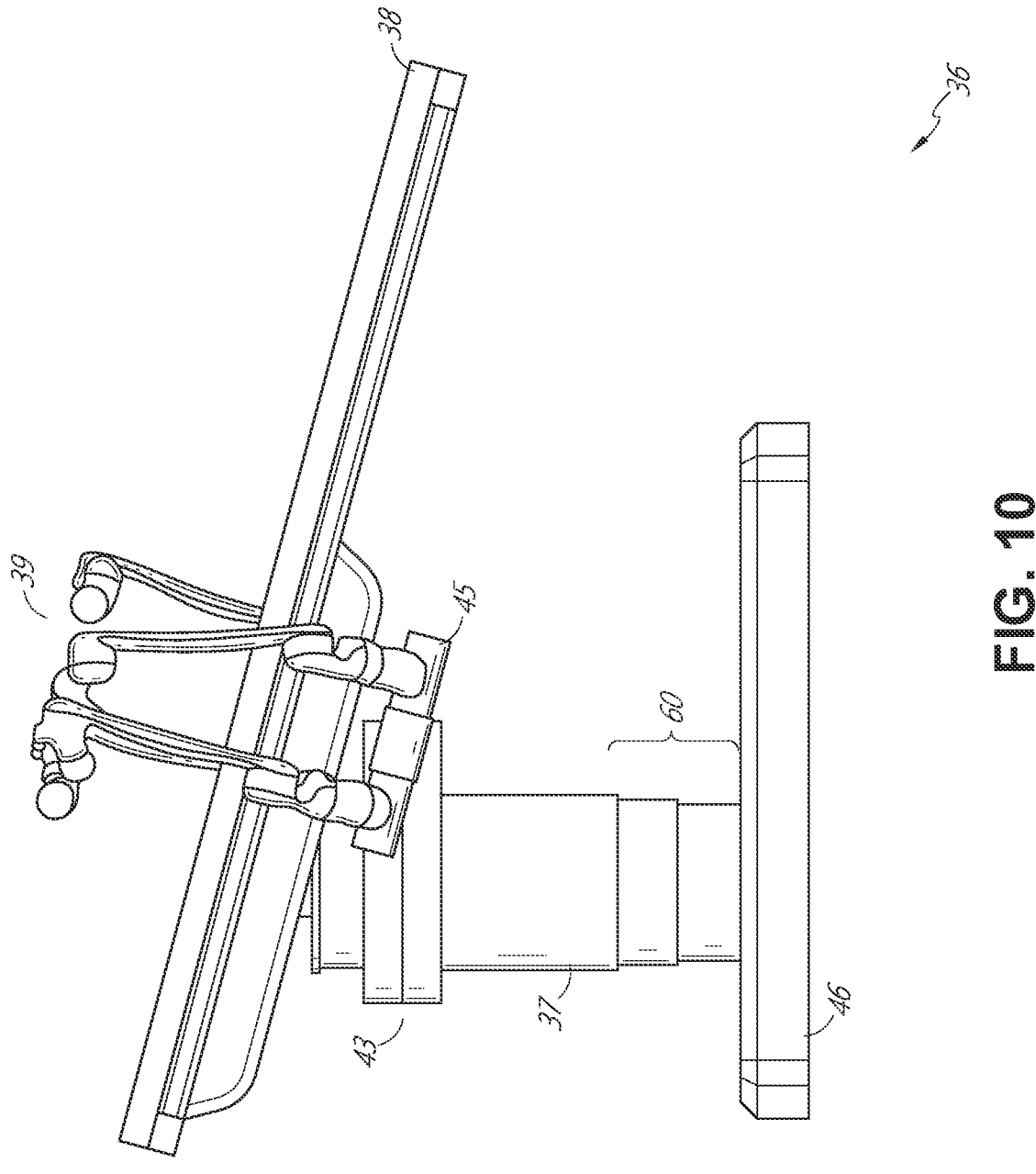
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
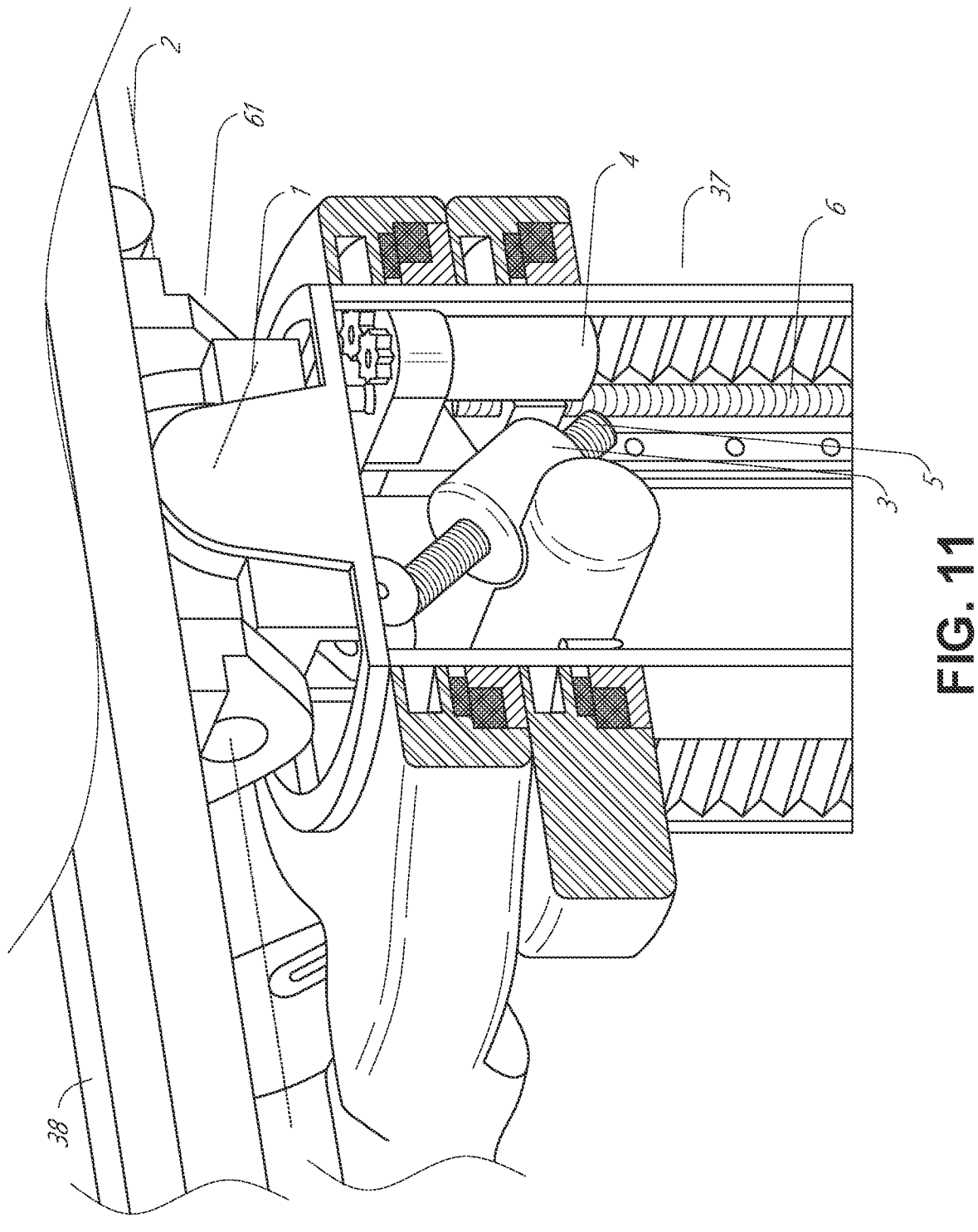
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
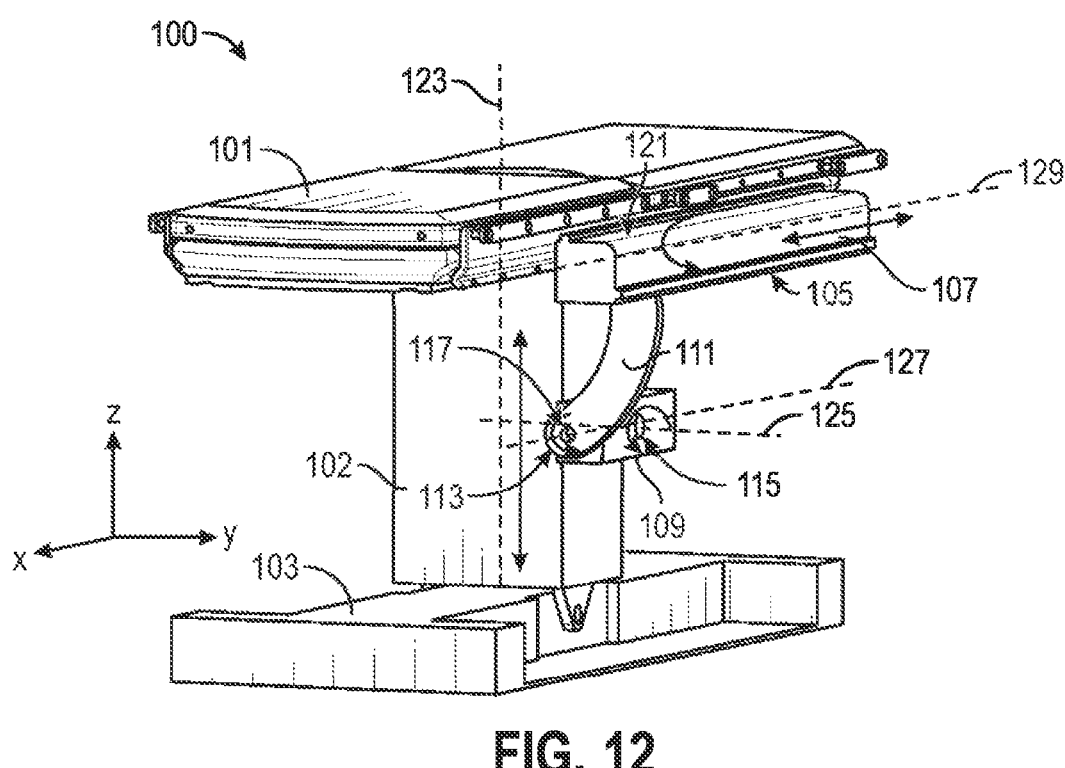
FIG. 12 illustrates an alternative embodiment of a table-based robotic system.
Figure 13:
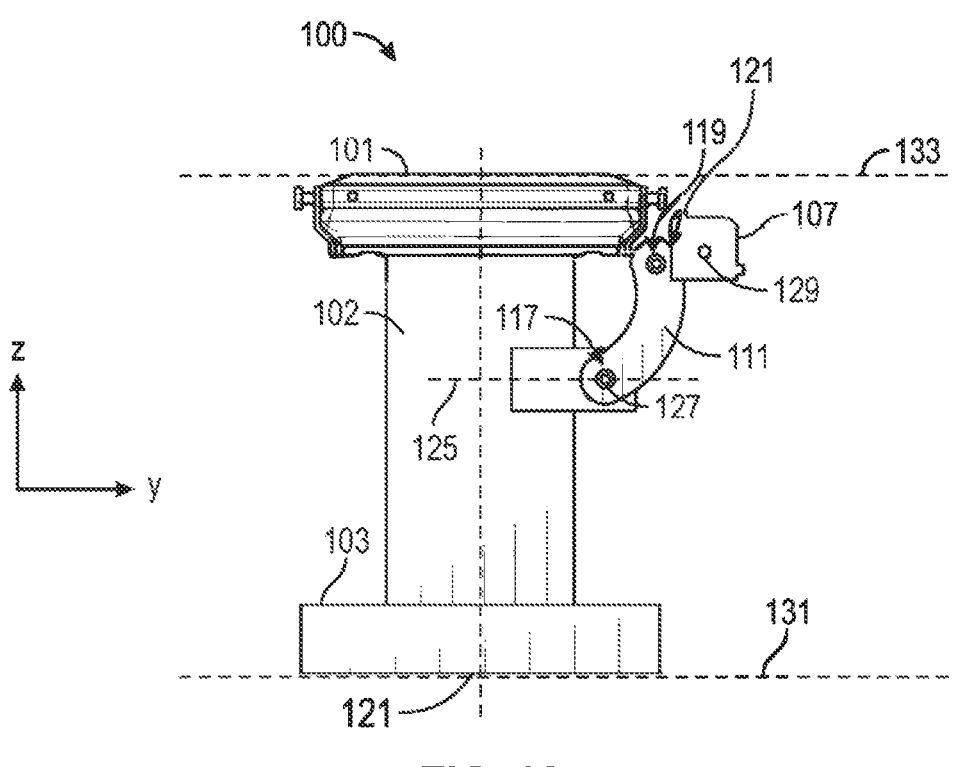
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
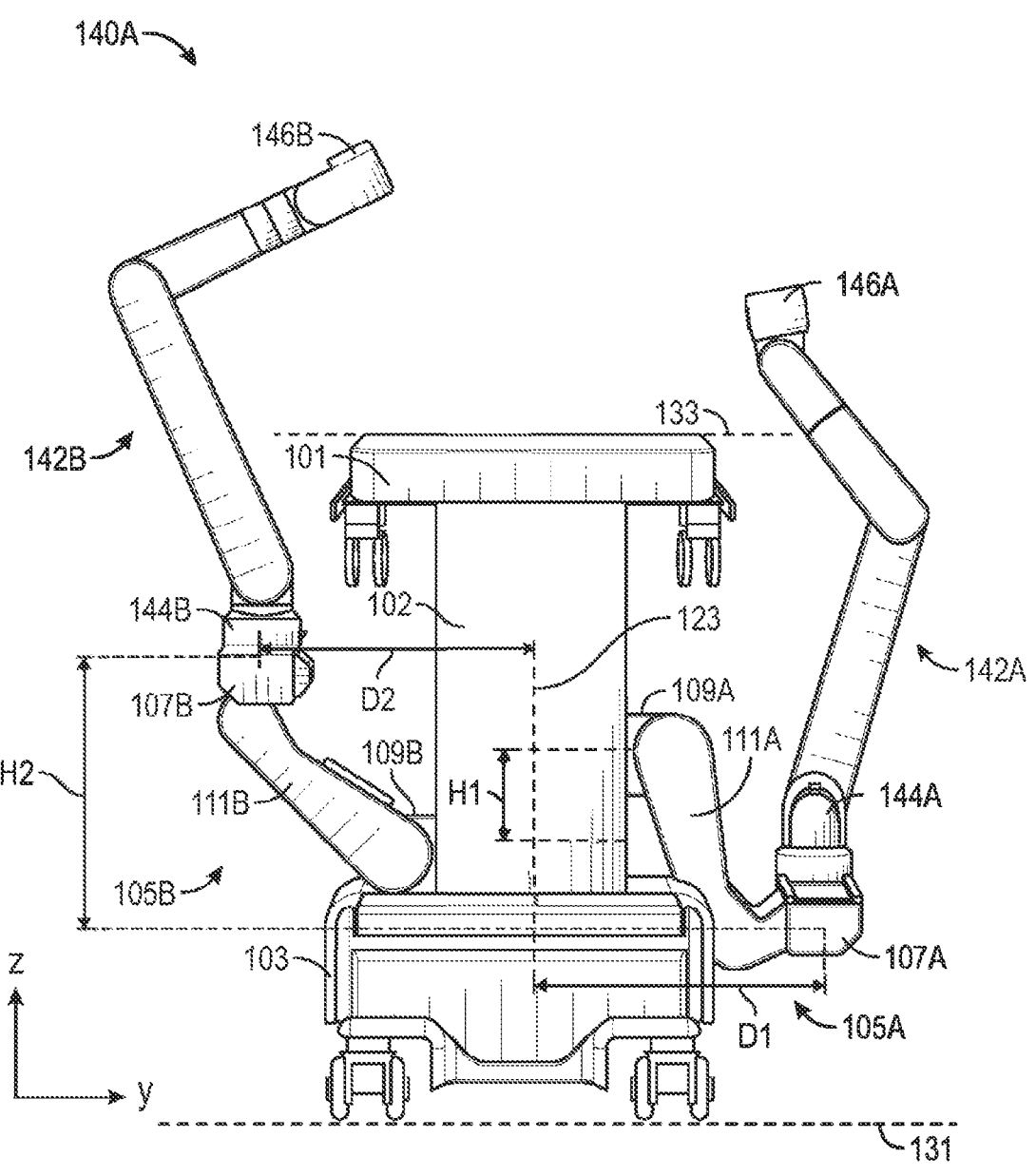
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (one degree of freedom, including insertion), a wrist (three degrees of freedom, including wrist pitch, yaw, and roll), an elbow (one degree of freedom, including elbow pitch), a shoulder (two degrees of freedom, including shoulder pitch and yaw), and base 144A, 144B (one degree of freedom, including translation).

In some embodiments, the insertion degree of freedom can be provided by the robotic arm 142A, 142B, while in other embodiments, the instrument itself provides insertion via an instrument-based insertion architecture.

C. Instrument Driver & Interface

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
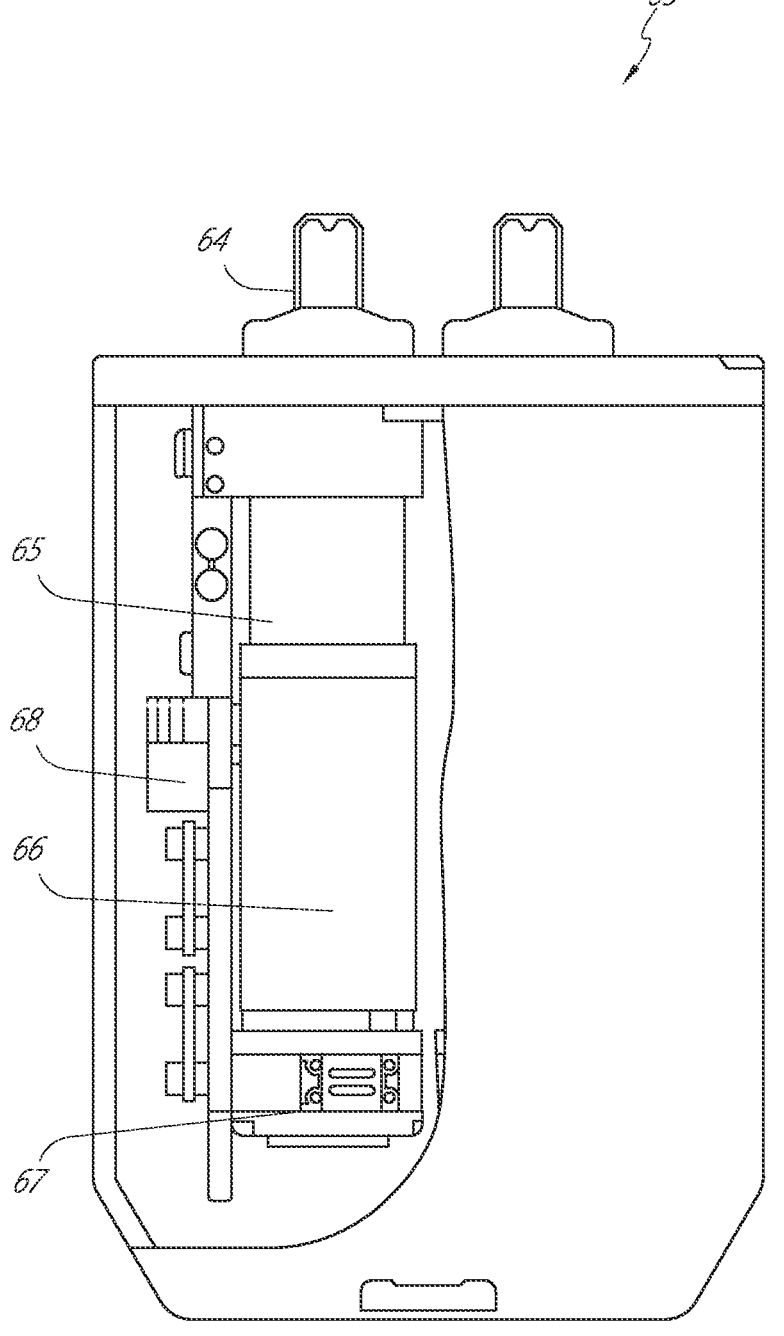
FIG. 15 illustrates an exemplary instrument driver.
Figure 15:

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument

Figure 16:
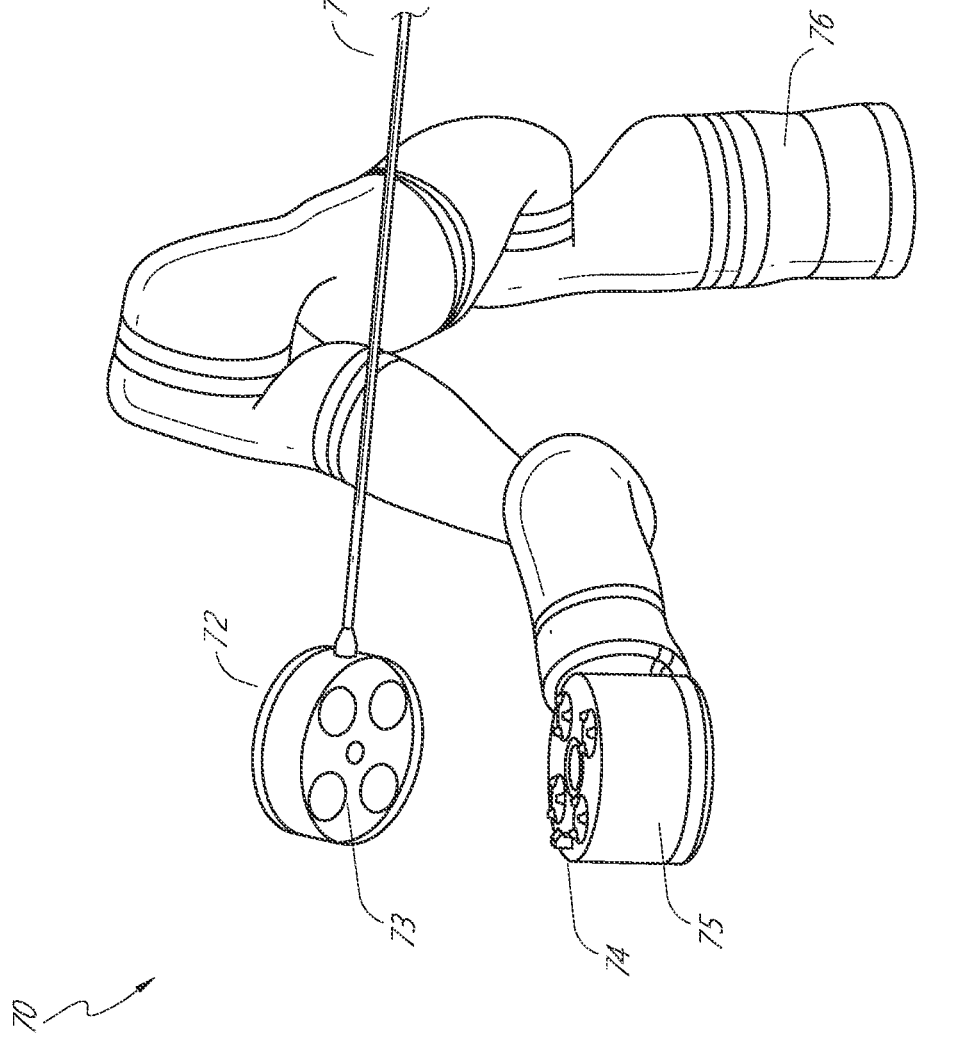
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires.

The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
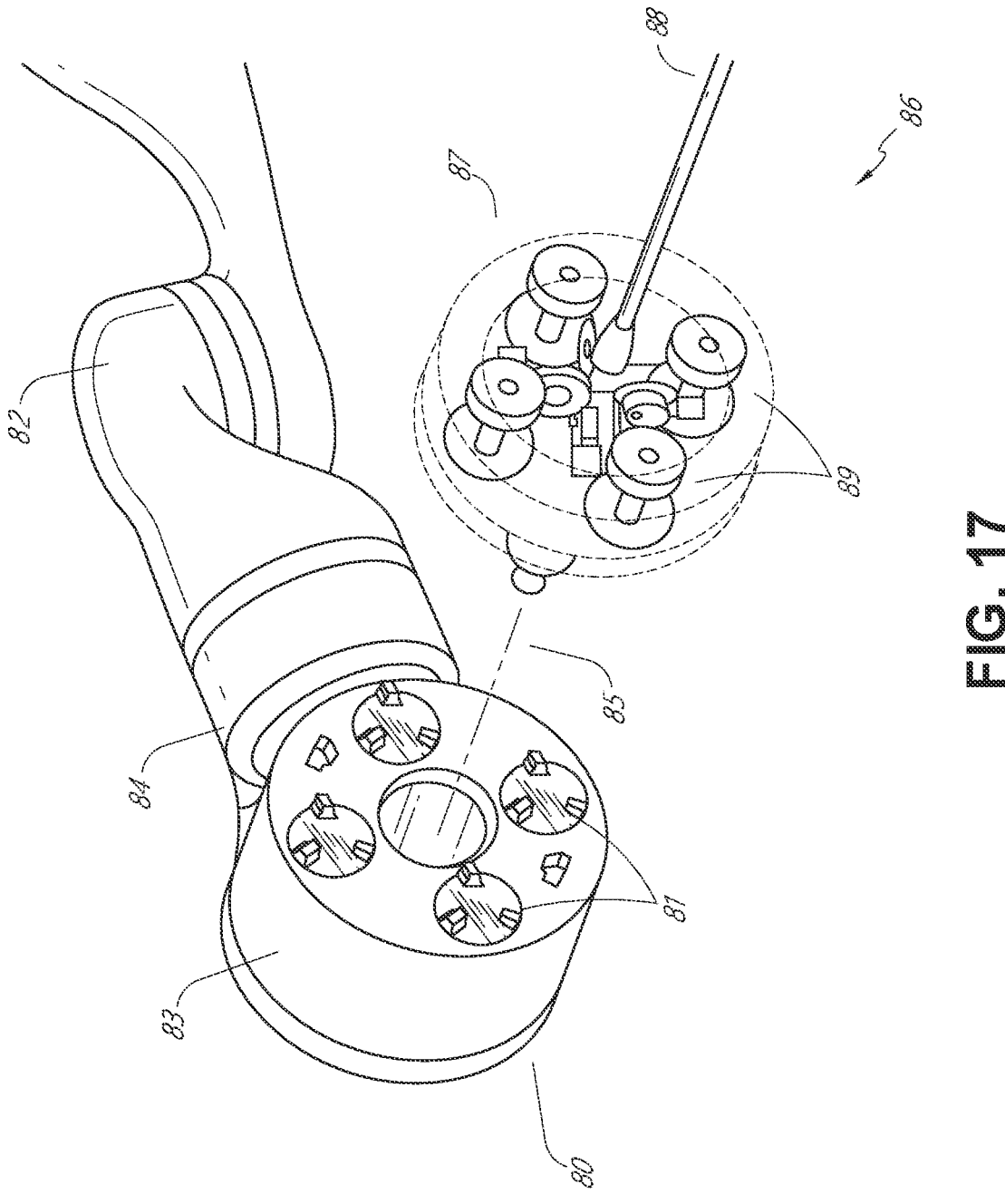
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs

89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
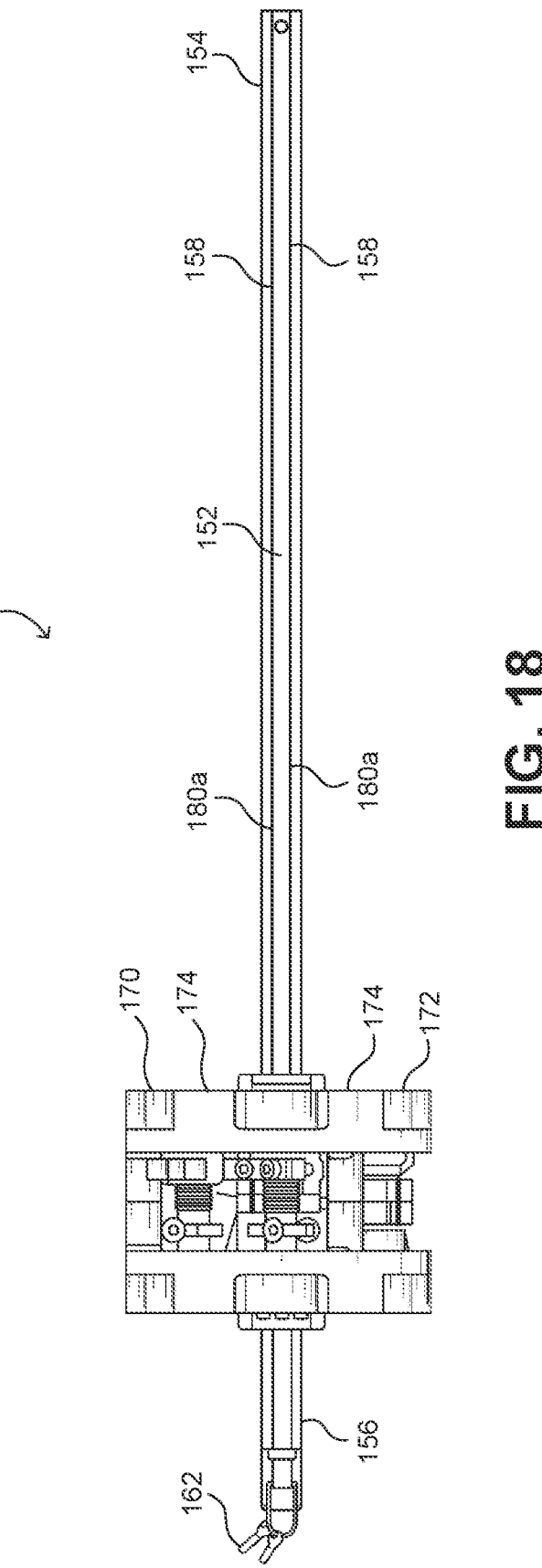
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
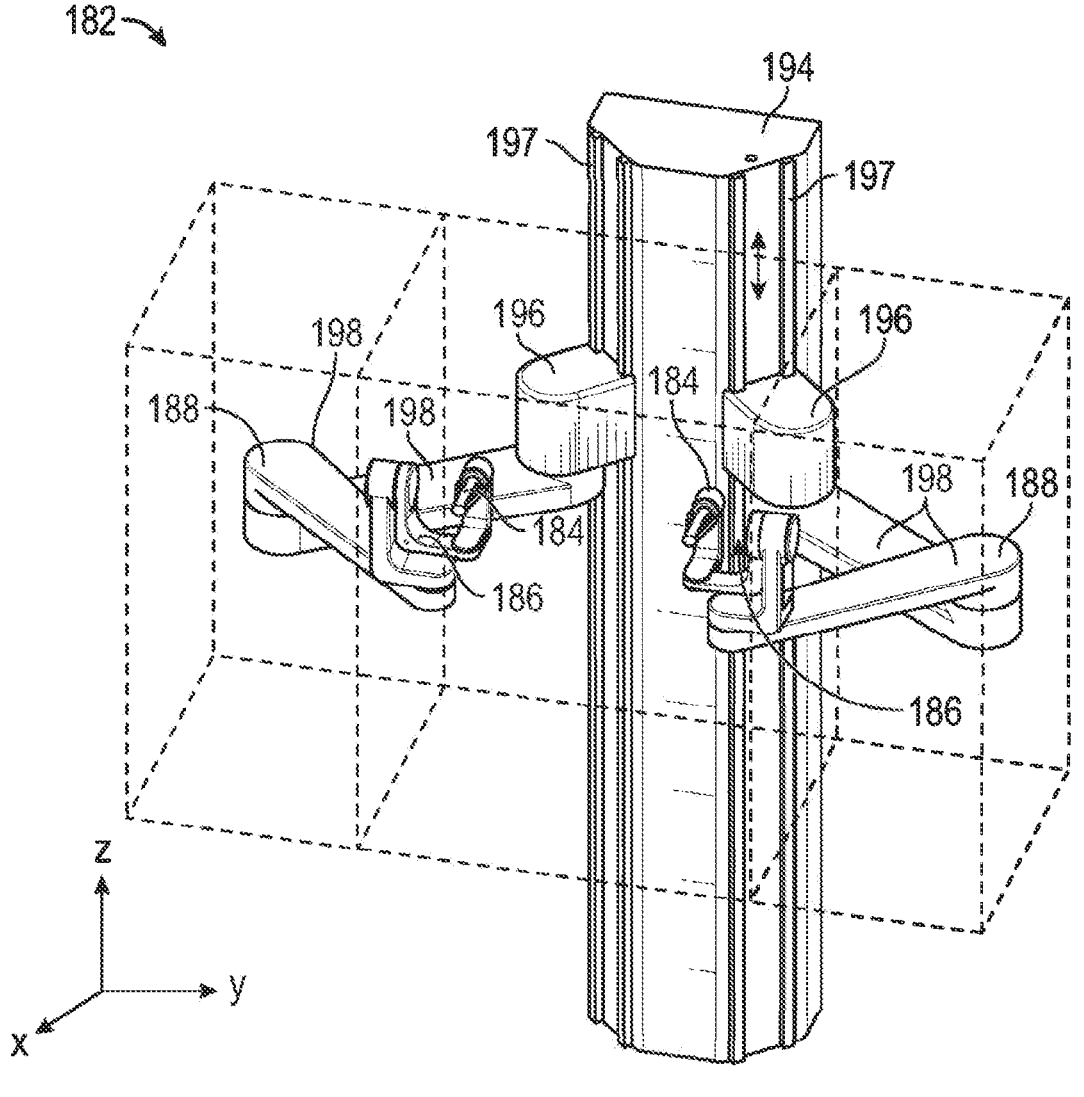
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control.

In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
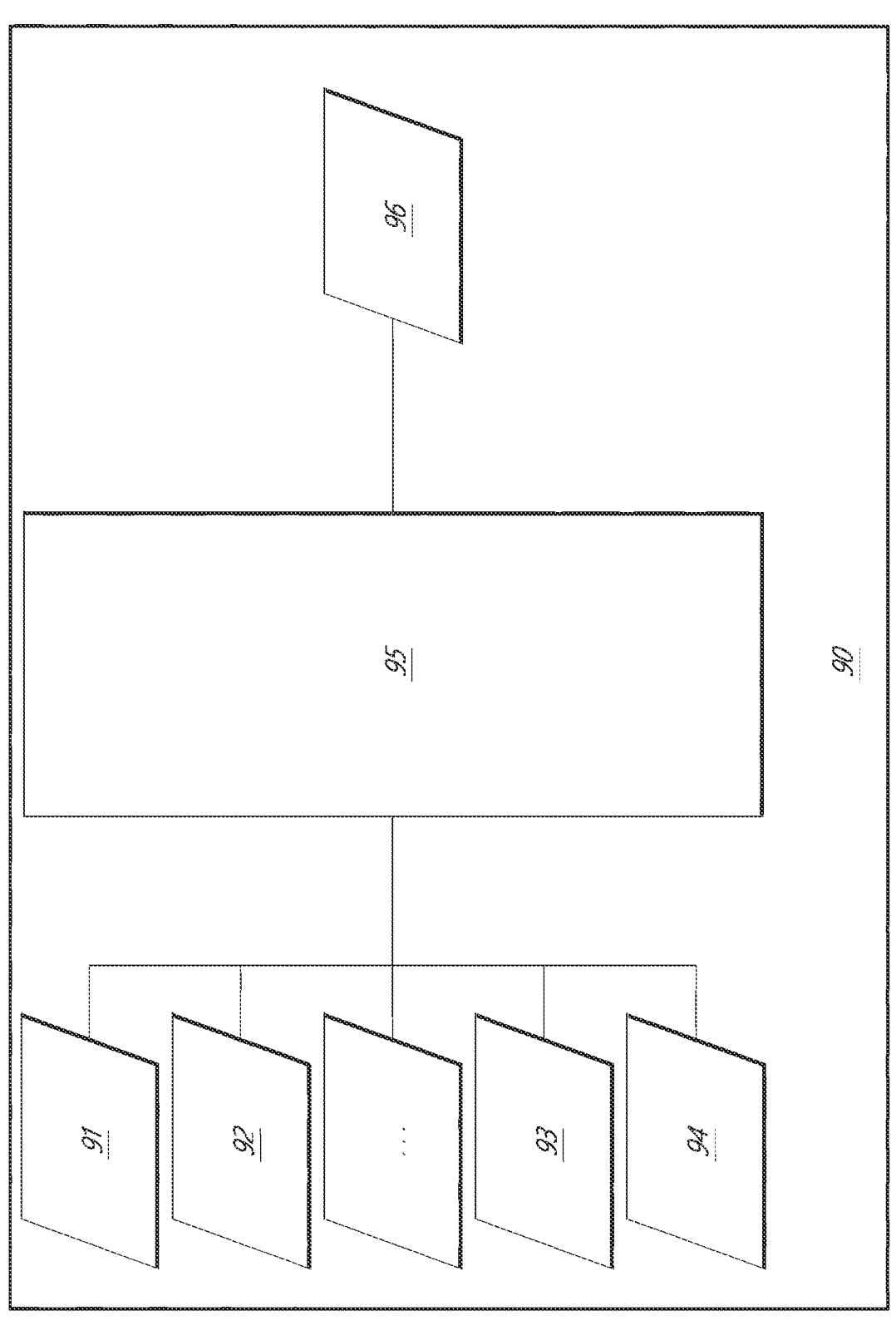
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

G. Tool Drivers with Axial Displacement Sensing

In accordance with some embodiments, robotic arms of the robotic system can be coupled to one or more tools, such as a cannula or other devices, that will be used to perform the surgical operation on a patient. Each robotic arm can include an instrument or tool driver to engage with a respective surgical tool. In some applications, surgical tools and/or sterile adapters can be attached or otherwise coupled to the tool driver by sliding the tool or adapter along a surface of the tool driver into engagement.

The tool driver can include one or more rotating outputs to manipulate or otherwise operate the surgical tool. The rotating outputs may be keyed to the mating inputs of the sterile adapter or the tool to allow for the transmission of torque.

The rotating outputs of the tool driver can retract axially to allow for the tool or a sterile adapter to slide along the surface of the tool driver to be coupled. The rotating outputs can extend axially to engage the mating inputs of the tool or sterile adapter upon proper engagement with the tool driver. In some applications, the rotating outputs can be rotated to align the keyed portions of the rotating outputs and the corresponding rotating inputs to allow for operation after attachment of the sterile adapter and tool to the tool driver. However, in certain robotic systems, it may be challenging to rapidly and accurately confirm that the rotating outputs of the tool driver are properly engaged with the rotating inputs of the sterile adapter and/or the surgical tool.

Figure 21:
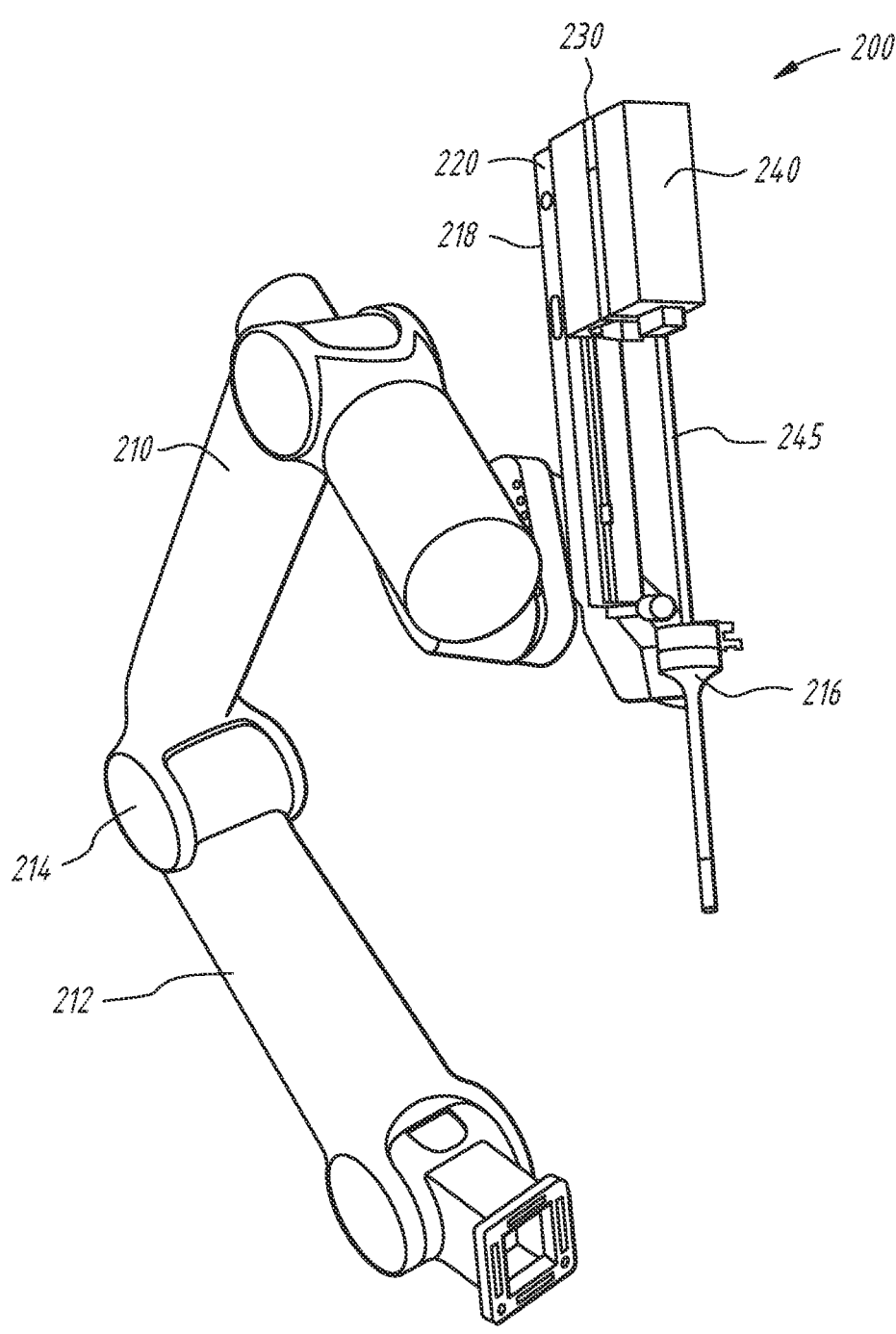
FIG. 21 illustrates a portion of a medical robotic system that includes an tool driver, in accordance with some embodiments.

FIG. 21 illustrates a portion of a medical robotic system 200 that includes an tool driver 220, in accordance with some embodiments. In the depicted example, the medical robotic system 200 can perform robotic surgery by operating a surgical tool 240 coupled to a robotic arm 210. During operation, the robotic arm 210 can move the surgical tool 240 to a desired location and orientation by manipulating a series of segments or links 212 connected to a series of joints 214. Each of the joints 214 can include an independent actuator with an independently controllable motor to control the positioning of the links 212 of the robotic arm 210.

As illustrated, the surgical tool 240 can be coupled to the robotic arm 210 via a stage 218 disposed at the distal end of the robotic arm 210. In some embodiments, the stage 218 can include a tool driver 220 to receive and operate the surgical tool 240. In some embodiments, the surgical tool 240 can be coupled directly to the tool driver 220. As illustrated, a sterile adapter 230 can be disposed between the surgical tool 240 and the tool driver 220. As described herein, the tool driver 220 can include one or more rotating outputs 224 (see FIG. 22) to control functions of the attached surgical tool 240. In the depicted example, the surgical tool 240 can be any suitable tool, including, but not limited to a laparoscopic tool such as a grasper or scissors. As illustrated, the surgical tool 240 can include a tool shaft 245 that extends through a lumen of a cannula 216 and into the patient.

Figure 22:
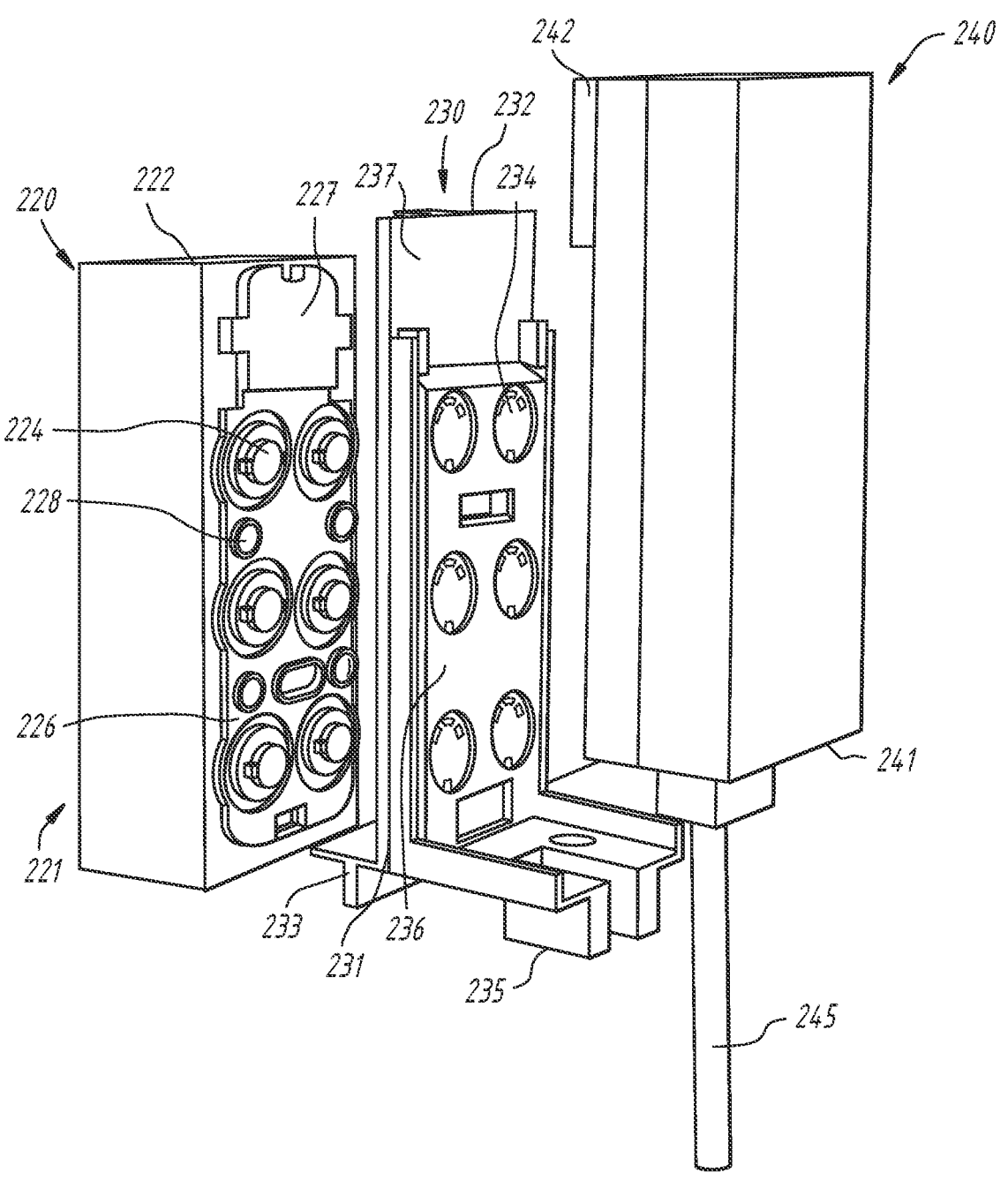
FIG. 22 illustrates an exploded assembly view of the tool driver, sterile adapter, and instrument of FIG. 21.
Figure 23:
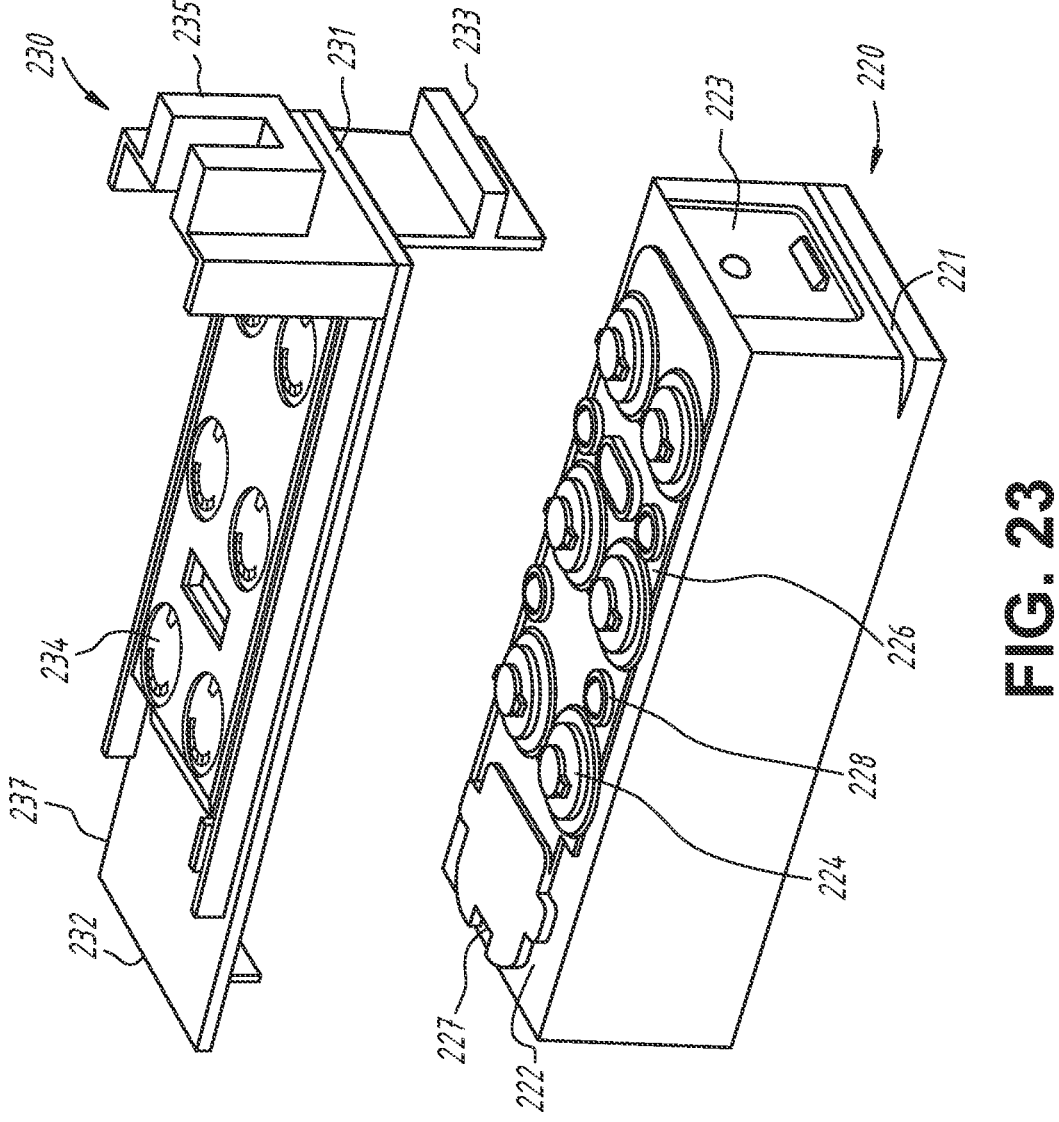
FIG. 23 illustrates an exploded assembly view of the tool driver and the sterile adapter of FIG. 21.
Figure 24:
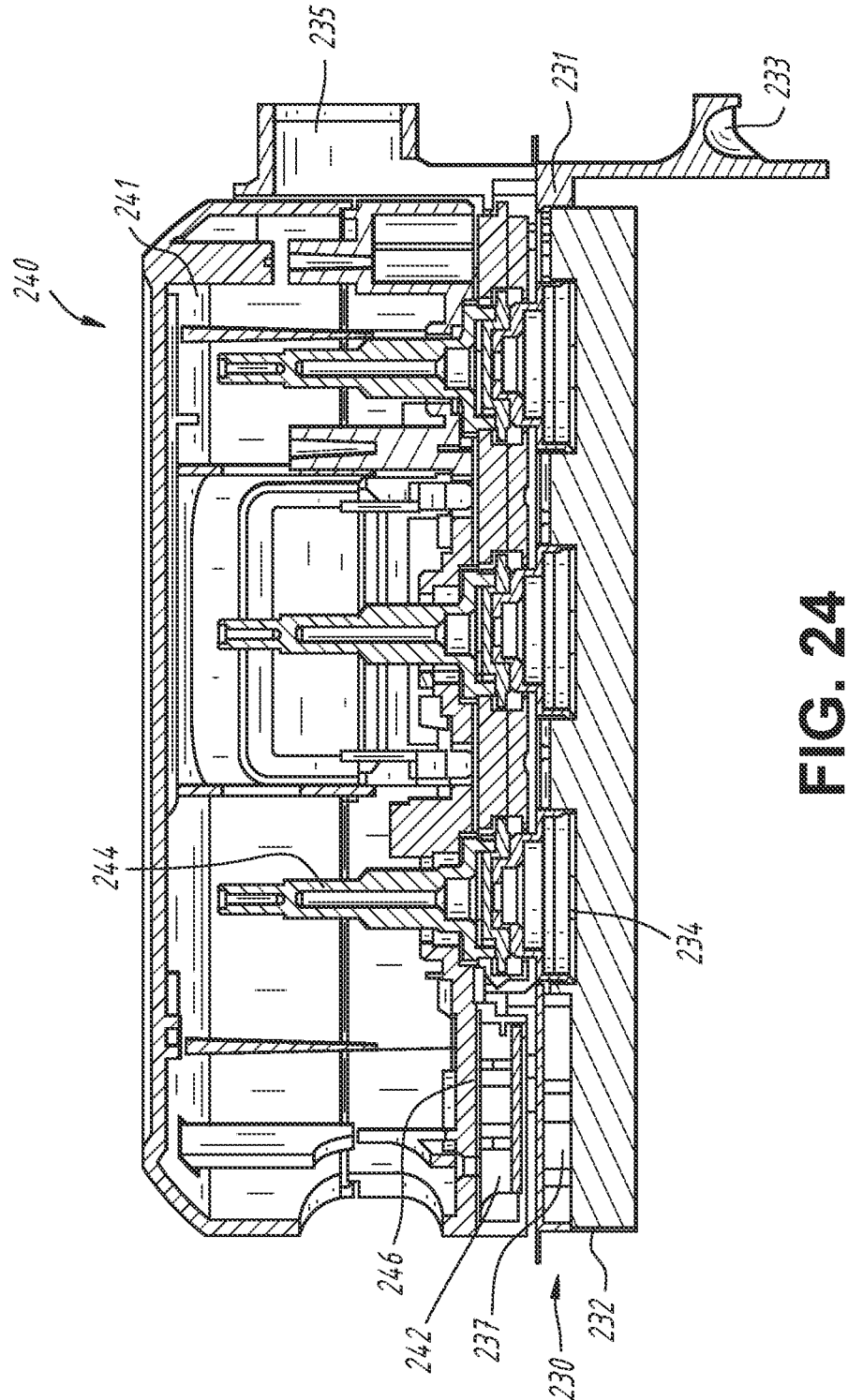
FIG. 24 illustrates a cross-sectional view of the instrument and the sterile adapter of FIG. 21.

FIG. 22 illustrates an exploded assembly view of the tool driver 220, sterile adapter 230, and instrument or surgical tool 240 of FIG. 21. FIG. 23 illustrates an exploded assembly view of the tool driver 220 and the sterile adapter 230 of FIG. 21. FIG. 24 illustrates a cross-sectional view of the surgical tool 240 and the sterile adapter 230 of FIG. 21. With reference to FIGS. 21-24, the tool driver 220 can be configured to operate mechanisms of the surgical tool 240 to control operation of the surgical tool 240. As illustrated, the tool driver 220 can provide an interface to receive and couple the surgical tool 240 to a robotic arm. During operation, the body 221 of the tool driver 220 can be coupled to the body 241 of the surgical tool 240 to allow the mating surface 226 of the tool driver 220 to be in contact with or adjacent to the mating surface 246 of the surgical tool 240. The mating surface 246 of the surgical tool 240 can be axially positioned into engagement with (or adjacent to) the mating surface 226 of the tool driver 220. In some embodiments, the mating surface 246 of the surgical tool 240 can be tilted or slid into engagement with mating surface 226 of the tool driver 220. The surgical tool 240 and/or the tool driver 220 can include engagement features 242, 222 to retain or attached the surgical tool 240 to the tool driver 220. As described herein, in some embodiments, a sterile adapter 230 can be disposed between the surgical tool 240 and tool driver 220 to provide a sterile barrier.

In the depicted example, the tool driver 220 can control operation of the attached surgical tool 240 via one or more drive outputs or rotating outputs 224. As illustrated, the one or more rotating outputs 224 of the tool driver 220 can operate one or more inputs 244 of the surgical tool 240. In some embodiments, inputs 244 of the surgical tool 240 can be coupled to pull wires, gears, screws, and/or other mechanisms to convert rotary motion of the inputs 244 to translational motion, rotary motion, articulating motion, or any other suitable motion of components of the surgical tool 240.

As illustrated, the tool driver 220 can include one or more rotating outputs 224 arranged with parallel axes to provide controlled torque to the inputs 244 of the surgical tool 240. Each of the rotating outputs 224 can include drive mechanism to transfer the torque to the respective input of the surgical tool 240. In some embodiments, the drive mechanism can include a motor to generate drive torque and a drivetrain to transfer torque to the respective input of the surgical tool 240. The drivetrain of the rotating output 224 can include one or more gears and a driveshaft. In some embodiments, each of the rotating outputs 224 can include an encoder to measure the rotational speed of the rotating output 224 and provide feedback to a control circuit to adjust operation of the drive mechanism. During operation, the control circuit may receive a control signal, energize a motor of the drive mechanism, compare the resulting motor speed measured by the encoder with the desired speed, and modulate the motor signal to generate the desired torque. In the depicted example, each rotating output 224 can be independently controlled and motorized.

As illustrated, the rotating outputs 224 of the tool driver 220 can be physically connected, latched, and/or coupled to the mating inputs 244 of the surgical tool 240 to allow the transfer of torque from the rotating outputs 224 to the mating inputs 244. The rotating outputs 224 can share axes of rotation with the inputs 244 of the surgical tool 240.

In some embodiments, the rotating outputs 224 can include features that engage or otherwise mate with corresponding features of the mating inputs 244. As illustrated, the rotating outputs 224 can be formed as disks that include keyed features that engage or otherwise mate with corresponding features of the mating inputs 244 to transfer torque. In some embodiments, the rotating outputs 224 includes or defines splines that are designed to mate with receptacles defined in the corresponding inputs 244.

Optionally, the features of the rotating outputs 224 may engage with the mating inputs 244 at one or more rotational orientations relative to a fixed reference point (e. g. at 0 degrees, 90 degrees, 180 degrees, and/or 270 degrees of rotation) to allow for the transfer of torque between the tool driver 220 and the surgical tool 240. In some applications, a rotating output 224 can be rotated until the features of the rotating output 224 align with and engage the features of the mating input 244, allowing torque to be transferred from the tool driver 220 and the surgical tool 240. Optionally, the rotating output 224 can be rotated either clockwise or counter-clockwise to seek alignment with the features of the mating input 244.

During operation, the rotating outputs 224 of the tool driver 220 can axially articulate or move relative to the mating surface 226 of the tool driver 220 to facilitate engagement or coupling of the tool driver 220 to a surgical tool 240 or other component. For example, one or more rotating outputs 224 can axially retract relative to the mating surface 226 to present a profile that does not impede engagement of the tool driver 220 with the surgical tool 240 or other components. In some applications, one or more rotating outputs 224 can retract to be flush with the mating surface 226. In some applications, one or more rotating outputs 224 may partially retract from an extended position but may extend beyond the mating surface 226. For example, one or more rotating outputs 224 can partially axially retract relative to the mating surface 226 to present a profile that does not impede engagement of the tool driver 220 with the surgical tool 240 when the features of the rotating outputs 224 are not rotationally aligned or engaged with the features of the mating inputs 244.

After the surgical tool 240 or other component is coupled to the tool driver 220, the rotating outputs 224 can axially extend toward the mating inputs 244 of the surgical tool 240 to facilitate operation of the surgical tool 240. The rotating outputs 224 can include a biasing member, such as a spring, to urge the rotating output 224 toward an extended position. In some applications, the rotating outputs 224 can extend toward and engage with the mating inputs 244. In some applications, one or more rotating outputs 224 may extend toward the mating inputs 244 but remain partially retracted relative to the mating surface 226 until the features of the rotating outputs 224 are rotationally aligned or engaged with the features of the mating inputs 244. In some embodiments, one or more rotating outputs 224 may extend and be rotationally aligned and engage with the mating inputs 244 of the surgical tool 240 but remain in a partially retracted position.

For procedures or applications that require a sterile environment, the robotic system 200 can include a sterile adapter 230 to provide a sterile barrier between the surgical tool 240 and the robotic arm 210. In the depicted example, the sterile adapter 230 includes a baseplate or floating plate 231 and a sterile drape disposed between the robotic arm 210 and the surgical tool 240 to provide a physical barrier. In some embodiments, a sterile drape can be coupled to the floating plate 231. In some embodiments, the sterile drape includes a thin, flexible material such as transparent or translucent plastic, is designed to cover the capital equipment, such as the tool driver 220, the robotic arm 210, and cart (in a cart-based system) or table (in a table-based system). Advantageously, the use of the sterile adapter allows for capital equipment such as the robotic arm 210 and the tool driver 220 to be positioned proximate to the patient while still being located in an area not requiring sterilization (i.e., non-sterile field). Further, on the other side of the sterile drape, the surgical tool 240 may interface with the patient in an area requiring sterilization (i.e., sterile field).

In the depicted example, the sterile adapter 230 can be coupled to the tool driver 220 and the surgical tool 240. In some embodiments, the sterile adapter 230 can be coupled to the tool driver 220 first and then the surgical tool 240 can be coupled to the sterile adapter 230 (and the attached tool driver 220). In some applications, the sterile adapter 230 can be coupled to the surgical tool 240 and then the surgical tool 240 (and the attached sterile adapter 230) can be coupled to the tool driver 220. As illustrated, the floating plate 231 of the sterile adapter 230 can be coupled to the body 221 of the tool driver 220 to allow the floating plate 231 to be in contact with or adjacent to the mating surface 226 of the tool driver 220. The floating plate 231 of the sterile adapter 230 can be axially positioned into engagement with (or adjacent to) the mating surface 226 of the tool driver 220. In some embodiments, the floating plate 231 of the sterile adapter 230 can be tilted or slid into engagement with mating surface 226 of the tool driver 220. In some embodiments, the sterile adapter 230 can include engagement features 232, 233 to engage with engagement features 222, 223 of the tool driver 220 to retain or attach the sterile adapter 230 to the tool driver 220. As illustrated, the engagement features 232, 233 can extend from the floating plate 231 of the sterile adapter 230.

In some applications, the tool driver 220 can align the floating plate 231 of the sterile adapter 230 relative to the mating surface 226 of the tool driver 220. As illustrated, the tool driver 220 can include one or more translatable pegs 228 extending perpendicularly from the mating surface 226. The translatable pegs 228 can include a biasing member to provide a biasing force away from the mating surface 226. During mating of the sterile adapter 230 with the tool driver 220, the translating pegs 228 can engage with or otherwise contact the floating plate 231 to align and/or space apart the floating plate 231 from the mating surface 226 into a desired orientation. In some embodiments, the translating pegs 228 can urge the floating plate 231 into a parallel alignment with the mating surface 226.

Further, the opposite side of the floating plate 231 of the sterile adapter 230 can be coupled to the body 241 of the surgical tool 240 to allow the floating plate 231 to be in contact with or adjacent to the mating surface 246 of the surgical tool 240. The mating surface 246 of the surgical tool 240 can be axially positioned into engagement with (or adjacent to) the floating plate 231 of the sterile adapter 230. In some embodiments, the mating surface 246 of the surgical tool 240 can be tilted or slid into engagement with the floating plate 231 of the sterile adapter 230. In some embodiments, the sterile adapter 230 can include engagement features 235 to engage with engagement features of the surgical tool 240 to retain or attach the surgical tool 240 to the sterile adapter 230. Similarly, the surgical tool 240 can include engagement features 242 to retain or attach the surgical tool 240 to the sterile adapter 230.

During operation, the sterile adapter 230 allows the surgical tool 240 to be operated through the sterile adapter 230 by the tool driver 220 to maintain physical separation, and thus sterility, between the surgical tool 240 and the tool driver 220 and the robotic arm 210. In the depicted example, the sterile adapter 230 includes one or more rotating passthroughs 234 to allow the rotating outputs 224 of the tool driver 220 to operate the corresponding inputs 244 of the surgical tool 240.

As illustrated, the one or more rotating outputs 224 of the tool driver 220 can operate one or more passthroughs 234 of the sterile adapter 230. The passthroughs 234 of the sterile adapter can be arranged with parallel axes to receive torque from the rotating outputs 224 of the tool driver. As illustrated, the passthroughs 234 of the sterile adapter 230 can be physically connected, latched, and/or coupled to the rotating outputs 224 of the tool driver 220 to allow the transfer of torque from the rotating outputs 224 to the passthroughs 234.

In some embodiments, the passthroughs 234 can include features that engage or otherwise mate with corresponding features of the rotating outputs 224. As illustrated, the passthroughs 234 can be formed as disks that include keyed features that engage or otherwise mate with corresponding features of the rotating outputs 224 to transfer torque. In some embodiments, the passthroughs 234 includes or defines splines that are designed to mate with receptacles defined in the corresponding rotating outputs 224.

Optionally, the features of the passthroughs 234 may engage with the rotating outputs 224 at one or more rotational orientations relative to a fixed reference point (e. g. at 0 degrees, 90 degrees, 180 degrees, and/or 270 degrees of rotation) to allow for the transfer of torque between the tool driver 220 and the sterile adapter 230. In some applications, a rotating output 224 can be rotated until the features of the rotating output 224 align with and engage the features of the passthroughs 234, allowing torque to be transferred from the tool driver 220 and the surgical tool 240. Optionally, the rotating output 224 can be rotated either clockwise or counter-clockwise to seek alignment with the features of the passthroughs 234.

Further, the opposite end of each of the passthroughs 234 of the sterile adapter 230 can operate one or more inputs 244 of the surgical tool 240. The passthroughs 234 of the sterile adapter can be arranged with parallel axes to transfer torque to the inputs 244 of the surgical tool 240. As illustrated, the passthroughs 234 of the sterile adapter 230 can be physically connected, latched, and/or coupled to the inputs 244 of the surgical tool 240 to allow the transfer of torque from the passthroughs 234 to the inputs 244 of the surgical tool 240.

In some embodiments, the passthroughs 234 can include features that engage or otherwise mate with corresponding features of the inputs 244. As illustrated, the passthroughs 234 can be formed as disks that include keyed features that engage or otherwise mate with corresponding features of the inputs 244 of the surgical tool 240 to transfer torque. In some embodiments, the passthroughs 234 includes or defines splines that are designed to mate with receptacles defined in the corresponding inputs 244.

Optionally, the features of the passthroughs 234 may engage with the inputs 244 at one or more rotational orientations relative to a fixed reference point (e. g. at 0 degrees, 90 degrees, 180 degrees, and/or 270 degrees of rotation) to allow for the transfer of torque between the sterile adapter 230 and the surgical tool 240. In some applications, a passthrough 234 can be rotated until the features of the passthroughs 234 align with and engage the features of the inputs 244, allowing torque to be transferred from the sterile adapter 230 and the surgical tool 240. Optionally, the passthroughs 234 can be rotated either clockwise or counter-clockwise to seek alignment with the features of the inputs 244.

During operation, the passthroughs 234 of the sterile adapter 230 can axially articulate or move relative to the mating surface 226 of the tool driver 220 and the mating surface 246 of the surgical tool 240 to facilitate engagement or coupling of the tool driver 220 to a surgical tool 240. For example, one or more passthroughs 234 can axially retract relative to the mating surface 226 to present a profile that does not impede engagement of the sterile adapter 230 with the tool driver 220. For example, one or more passthroughs 234 can partially axially retract relative to the mating surface 226 to present a profile that does not impede engagement of the sterile adapter 230 with the tool driver 220 when the features of the rotating outputs 224 are not rotationally aligned or engaged with the features of the passthroughs 234.

Similarly, one or more passthroughs 234 can axially retract relative to the mating surface 246 to present a profile that does not impede engagement of the sterile adapter 230 with the surgical tool 240. For example, one or more passthroughs 234 can partially axially retract relative to the mating surface 246 to present a profile that does not impede engagement of the sterile adapter 230 with the surgical tool 240 when the features of the inputs 244 are not rotationally aligned or engaged with the features of the passthroughs 234.

In some embodiments, the passthroughs 234 of the sterile adapter 230 may be biased toward a neutral position between the surgical tool 240 and the tool driver 220. Optionally, the passthroughs 234 may be coupled to the floating plate 231 with a resilient material that allows for axial displacement but biases the passthroughs 234 toward a neutral position relative to the floating plate 231. In some applications, the passthroughs 234 may move toward a neutral position after engaging with features of the rotating outputs 224 and/or inputs 244.

An example process of attaching the surgical tool 240 to the tool driver 220 is described herein. First, the sterile adapter 230 can be coupled to the tool driver 220. The rotating outputs 224 of the tool driver 220 can retract to allow the floating plate 231 of the sterile adapter 230 to slide past or otherwise couple with the mating surface 226 of the tool driver 220. In some applications, after the sterile adapter 230 is coupled to the tool driver 220, the rotating outputs 224 of the tool driver 220 may not be rotationally aligned with the passthroughs 234, depressing or otherwise forcing the rotating outputs 224 to remain in a retracted position. After coupling the sterile adapter 230 to the tool driver 220, the rotating outputs 224 can be rotated until they axially extend and engage with the passthroughs 234 of the sterile adapter 230.

Next, the surgical tool 240 can be coupled to the tool driver 220 via the sterile adapter 230. The rotating outputs 224 of the tool driver 220 along with the passthroughs 234 of the sterile adapter 230 can retract to allow the mating surface 246 of the surgical tool 240 to slide past or otherwise couple to the floating plate 231 of the sterile adapter 230. In some applications, after the surgical tool 240 is coupled to the tool driver 220, the passthroughs 234 of the sterile adapter 230 (and the rotating outputs 224 of the tool driver 220) may not be rotationally aligned with the inputs 244 of the surgical tool 240, depressing or otherwise forcing the rotating outputs 224 to remain in a retracted position. After coupling the surgical tool 240 to the tool driver 220, the rotating outputs 224 can be rotated until the passthroughs 234 of the sterile adapter 230 engage with the rotating inputs 244 of the surgical tool 240, allowing the passthroughs 234 (and the rotating outputs 224) to axially extend. In some embodiments, the rotating outputs 224 can be "homed" to calibrate the tool driver 220 with the attached surgical tool 240.

In some applications, the surgical tool 240 can be removed from the tool driver 220 by depressing or otherwise activating a release mechanism, releasing engagement features 222, 242 between the surgical tool 240 and the tool driver 220. Similarly, the sterile adapter 230 can be removed from the tool driver 220 by depressing or otherwise activating a release mechanism, releasing engagement features 232, 233 between the sterile adapter 230 and the tool driver 220.

H. Inductance Based Displacement Sensing

In the depicted example, the robotic system 200 can detect if a surgical tool 240 is properly or fully engaged with the tool driver 220. For example, the robotic system 200 can detect if tool driver 220 and the rotating outputs 224 are properly engaged with the sterile adapter 230 and/or the surgical tool 240 during each stage of engagement. In some applications, the robotic system 200 can detect if the rotating outputs 224 are rotationally or otherwise fully engaged with the passthroughs 234 of the sterile adapter 230. Similarly, in some applications, the robotic system 200 can detect if the rotating outputs 224 (and/or the engaged passthroughs 234 of the sterile adapter 230) are rotationally or otherwise fully engaged with the inputs 244 of the surgical tool 240. Further, in some applications, the robotic system 200 can detect the axial position (depression/extension) of the floating plate 231 of the sterile adapter 230 relative to the mating surface 226 of the tool driver 220.

As described herein, the robotic system 200 can utilize the axial position of the rotating outputs 224 to determine the engagement of the tool driver 220 with the sterile adapter 230 and/or the surgical tool 240. In some embodiments, the tool driver 220 can include one or more sensors to detect the axial position of the rotating outputs 224. Advantageously, by detecting the axial position of the rotating outputs 224, the robotic system 200 and/or the clinician can rapidly and accurately determine if the tool driver 220 (and the rotating outputs 224) are properly engaged with the sterile adapter 230 and/or the surgical tool 240. Further, the robotic system 200 and/or the clinician can rotate the rotating outputs 224 of the tool driver 220 based on the axial position feedback to rapidly and accurately engage the rotating outputs 224 with the passthroughs 234 of the sterile adapter 230 and engage the passthroughs 234 with the inputs 244 of the surgical tool 240.

Figure 25:
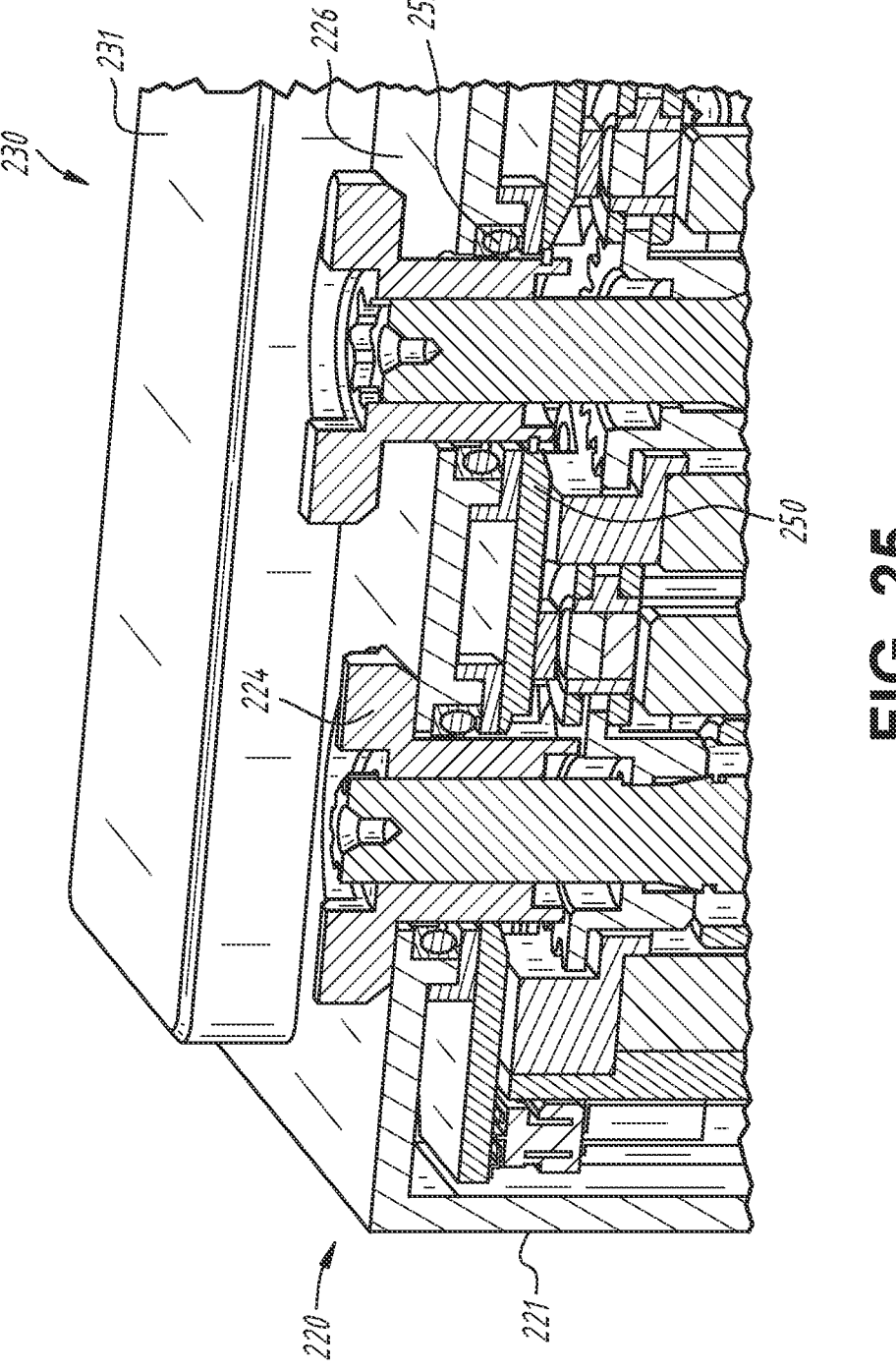
FIG. 25 illustrates a cross-sectional view of the tool driver and the sterile assembly of FIG. 21.

FIG. 25 illustrates a cross-sectional view of the tool driver 220 and the sterile adapter 230 of FIG. 21. With reference to FIG. 25, the tool driver 220 includes one or more position sensors 250 to detect the axial position of a respective rotating output 224. In the depicted example, the position sensor 250 provides a signal to the robotic system 200 corresponding to the axial position of a respective rotating output 224.

In some embodiments, the position sensor 250 can measure inductance or change in inductance to provide a position signal to the robotic system 200. The position sensor 250 can include a coil to detect inductance. In some applications, the change in position of the shaft of the rotating output 224 relative to the coil (or position sensor 250 generally) can change the inductance of the coil of the position sensor 250. The coil can be disposed around a shaft of the rotating output 224. The coil can be a wire wound coil or a coil disposed on a printed circuit board. Optionally, the rotating output 224 can include a ferrous component 252 to increase or intensify the inductance of the position sensor 250.

Figure 26:
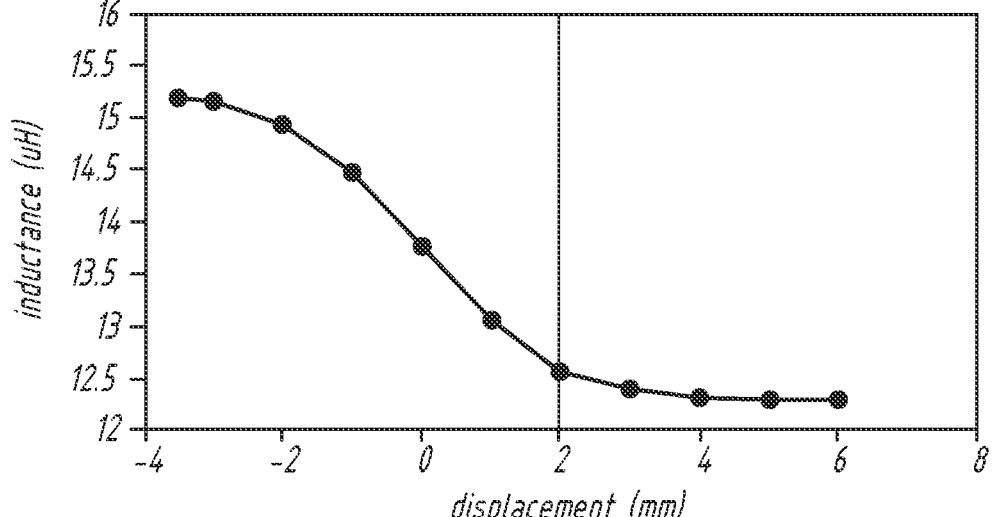
FIG. 26 is a chart illustrating axial displacement of a rotating output of the tool driver against an inductance value of a sensor of the tool driver, in accordance with some embodiments.

FIG. 26 is a chart illustrating axial displacement of a rotating output 224 of the tool driver 220 against an inductance value of a sensor 250 of the tool driver 220, in accordance with some embodiments. As illustrated, the robotic system 200 can correspond the inductance value received by the position sensor 250 with the axial displacement of the rotating output 224. In some embodiments, the inductance value received from the position sensor 250 can be measured or converted by an integrated circuit and relevant support circuitry to displacement data.

I. Optical Based Displacement Sensing

Figure 27:
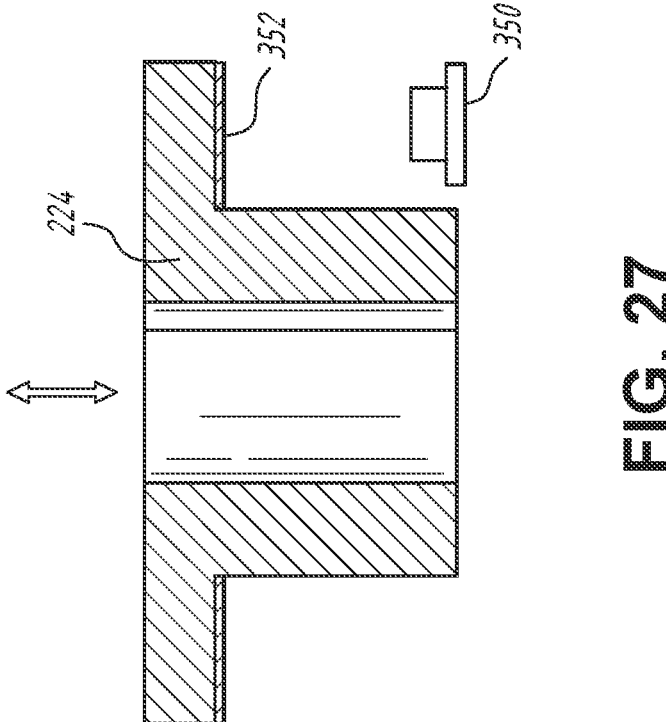
FIG. 27 illustrates a rotating output of an tool driver with an optical sensor, in accordance with some embodiments.

FIG. 27 illustrates a rotating output 224 of an tool driver 220 with an optical sensor 350, in accordance with some embodiments. With reference to FIG. 27, the tool driver 220 includes one or more optical sensors 350 to detect the axial position of a respective rotating output 224. In the depicted example, the optical sensor 350 provides a signal to the robotic system 200 corresponding to the axial position of a respective rotating output 224.

In some embodiments, the optical sensor 350 can emit light toward the rotating output 224 and measure the amount of reflected light to provide a position signal to the robotic system 200. During operation, the change in position of the rotating output 224 relative to the optical sensor 350 can change the amount of light received by the optical sensor 350. In some embodiments, the optical sensor 350 can emit a pulse of light and measure the "time of flight" for the pulse to return to the optical sensor 350 to provide a position signal to the robotic system 200. During operation, the change in position of the rotating output 224 relative to the optical sensor 350 can change the amount of time required to reflect the light pulse back to the optical sensor 350. The optical sensor 350 can be disposed below a flat surface of the rotating output 224. Optionally, the flat surface of the rotating output 224 can include a reflective surface 352 to increase, intensify, or otherwise facilitate the reflection of light to the optical sensor 350.

Figure 28:
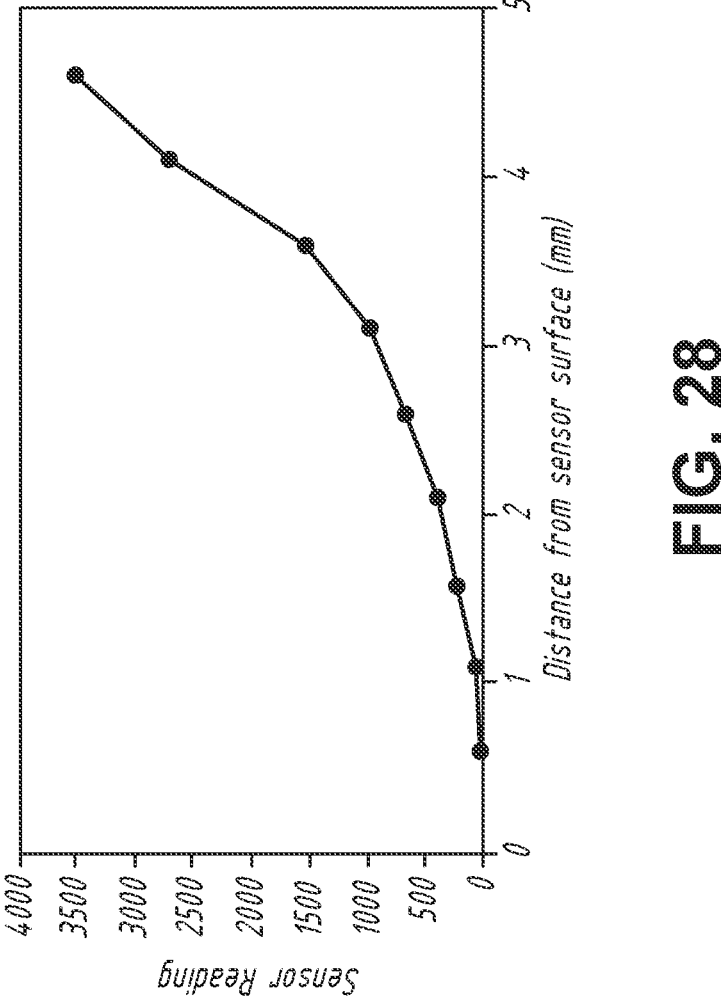
FIG. 28 is a chart illustrating axial displacement of a rotating output of the tool driver against a sensor reading of the optical sensor of FIG. 27, in accordance with some embodiments.

FIG. 28 is a chart illustrating axial displacement of a rotating output 224 of the tool driver 220 against a sensor reading of the optical sensor 350 of FIG. 27, in accordance with some embodiments. As illustrated, the robotic system 200 can correspond the sensor value received by the optical sensor 350 with the axial displacement of the rotating output 224. In some embodiments, the sensor value (either amount of light received or time of flight data) received from the optical sensor 350 can be measured or converted by an integrated circuit and relevant support circuitry to displacement data.

As described herein, the displacement data from the sensors 250, 350 can be utilized by the robotic system 200 to determine if tool driver 220 and the rotating outputs 224 are properly engaged with the sterile adapter 230 and/or the surgical tool 240 during each stage of engagement. For example, the displacement data from the sensors 250, 350 can be utilized by the robotic system 200 to detect the axial position (depression/extension) of the floating plate 231 of the sterile adapter 230 relative to the mating surface 226 of the tool driver 220.

In some applications, the displacement data from the sensors 250, 350 can be utilized by the robotic system 200 to determine if the rotating outputs 224 are aligned with and engaged with the features of the passthrough 234 of the sterile adapter 230 and if the passthroughs 234 are aligned with engaged with the features of the mating inputs 244 of the surgical tool 240.

Further, in some applications, the displacement data from the sensors 250, 350 can be utilized by the robotic system 200 to control the rotation of the rotating outputs 224 to facilitate the engagement of the rotating outputs 224 with the passthroughs 234 of the sterile adapter 230 and the engagement of the rotating outputs 224 (via passthroughs 234) with the inputs 244 of the surgical tool 240. For example, the rotating outputs 224 can be rotated until they are axially extended to engage the passthroughs 234 and/or the passthroughs 234 are engaged with the inputs 244 of the surgical tool 240. The robotic system 200 may use sensor feedback and displacement data to rotate the rotating outputs 224 clockwise or counter-clockwise to seek alignment with the features of the passthrough 234 and/or input 244. In some applications, the rotating outputs 224 may seek alignment between two or more rotational orientations relative to a fixed reference point (e. g. at 0 degrees, 90 degrees, 180 degrees, and/or 270 degrees of rotation).

2. Implementing Systems and Terminology

Implementations disclosed herein can advantageously provide systems, methods and apparatus for provide an added level of safety to a robot that interacts with humans, by allowing joints to be completely unlocked and repositioned even under complete electrical or software failure of the robot.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present inventions. Various modifications to these implementations will be readily apparent to those skilled in the art, and the generic principles defined herein may be applied to other implementations without departing from the scope of the inventions. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present inventions are not intended to be limited to the implementations shown herein but is to be accorded the widest scope consistent with the principles and novel features disclosed herein.

What is claimed is:

1. A tool driver for a surgical robotic system, the tool driver comprising:
   a body;
   a rotating output extending from the body, the rotating output being axially translatable relative to a surface of the body along an axis perpendicular to the surface of the body, the rotating output being configured to engage with an input of a surgical tool;
   a drive mechanism coupled to the rotating output, the drive mechanism being configured to rotate the rotating output about the axis; and
   a sensor coupled to the body and configured to determine an axial position of the rotating output relative to the body.

2. The tool driver of claim 1, wherein the drive mechanism comprises a motor coupled to the rotating output.

3. The tool driver of claim 1, wherein the rotating output comprises a disk extending from the body, the disk being configured to engage with the input of the surgical tool.

4. The tool driver of claim 3, wherein the disk defines a keyed portion configured to transfer torque from the rotating output to the input of the surgical tool.

5. The tool driver of claim 1, further comprising a biasing member coupled to the rotating output and configured to apply a biasing force to the rotating output along the axis and away from the body.

6. The tool driver of claim 1, wherein the sensor further comprises an inductive sensor configured to receive a signal from a component.

7. The tool driver of claim 6, wherein the rotating output further comprises a ferrous component, the inductive sensor further comprises a conductive coil, and axial movement of the ferrous component relative to the conductive coil changes an inductance of the conductive coil providing a signal corresponding to the axial movement of the rotating output to a controller.

8. The tool driver of claim 1, wherein the sensor comprises an optical sensor.

9. The tool driver of claim 8, wherein the rotating output comprises a reflective surface configured to provide a signal to the optical sensor.

10. The tool driver of claim 1, wherein the body is configured to couple to a sterile adapter, the tool driver further comprising a translatable peg extending perpendicular to the surface of the body, wherein the translatable peg is urged away from the body to space apart the sterile adapter from the body.

11. The tool driver of claim 1, further comprising a plurality of rotating outputs.

12. A method of operating a surgical robotic system, the method comprising:

receiving coupling of a mating device to a tool driver, the tool driver comprising a body and a rotating output that is rotatable relative to the body, the mating device comprises a corresponding input;

axially urging the rotating output away from the body and toward the corresponding input;

rotating the rotating output relative to the corresponding input; and detecting an axial position of the rotating output.

13. The method of claim 12, further comprising: determining engagement between the rotating output and the corresponding input based on the axial position of the rotating output.

14. The method of claim 12, further comprising determining engagement between the mating device and the tool driver based on the axial position of the rotating output.

15. The method of claim 12, wherein detecting the axial position of the rotating output further comprises detecting an inductance value to determine the axial position of the rotating output.

16. The method of claim 12, wherein detecting the axial position of the rotating output further comprises detecting a light signal to determine the axial position of the rotating output.

17. The method of claim 12, wherein the mating device comprises a sterile adapter comprising a sterile adapter input and a floating plate mechanically constraining the sterile adapter input, the method further comprising:

determining an axial position of the floating plate based on the axial position of the rotating output.

18. The method of claim 17, further comprising: determining a latch state of the floating plate based on the axial position of the rotating output.

19. A surgical robotic system comprising:

a tool driver comprising:

a body;

a rotating output extending from the body, the rotating output defining a profile, the rotating output being axially translatable along an axis perpendicular to a surface of the body and rotatable about the axis; and a sensor coupled to the body and configured to determine an axial position of the rotating output relative to the body; and a surgical tool comprising:

a movable tool portion; and an input configured to move the tool portion, the input defining a mating profile, wherein the surgical tool is configured to be coupled to the tool driver to permit the rotating output to translate toward the input of the surgical tool, and the sensor is further configured to determine rotational engagement between the profile of the rotating output and the mating profile of the input of the surgical tool.

20. The surgical robotic system of claim 19, further comprising:

a sterile adapter comprising:

a movable baseplate; and a rotating passthrough defining a tool driver profile on a first side and a tool profile on an opposing second side, wherein the rotating passthrough is axially translatable along a passthrough axis perpendicular to the movable baseplate and rotatable about the axis, wherein the sterile adapter is configured to be coupled to the tool driver and the surgical tool to permit the rotating output of the tool driver to translate toward the rotating passthrough of the sterile adapter and translate the rotating passthrough toward the input of the tool portion, and the sensor is further configured to determine rotational engagement between the profile of the rotating output and the tool driver profile of the rotating passthrough.

21. The surgical robotic system of claim 20, wherein the sensor is further configured to determine rotational engagement between the tool profile of the rotating passthrough and the mating profile of the input of the surgical tool.

*    *    *    *    *